US012806202B2

(12) United States Patent
Samatar et al.

(10) Patent No.: US 12,806,202 B2
(45) Date of Patent: Nov. 24, 2026

(54) COMBINATIONS OF WEE1 INHIBITORS AND Bcl-2 INHIBITORS FOR TREATMENT OF CANCER

(71) Applicant: Recurium IP Holdings, LLC, San Diego, CA (US)

(72) Inventors: Ahmed Abdi Samatar, West Windsor, NJ (US); Jiali Li, San Diego, CA (US); Hooman Izadi, San Diego, CA (US); Peter Qinhua Huang, San Diego, CA (US); Joseph Robert Pinchman, San Diego, CA (US); Brant Clayton Boren, San Diego, CA (US); Kevin Duane Bunker, Escondido, CA (US); Fernando Donate, Santa Monica, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 890 days.

(21) Appl. No.: 17/757,530

(22) PCT Filed: Dec. 16, 2020

(86) PCT No.: PCT/US2020/065410
§ 371 (c)(1),
(2) Date: Jun. 16, 2022

(87) PCT Pub. No.: WO2021/127045
PCT Pub. Date: Jun. 24, 2021

(65) Prior Publication Data

US 2023/0054854 A1 Feb. 23, 2023

Related U.S. Application Data

(60) Provisional application No. 62/952,032, filed on Dec. 20, 2019.

(51) Int. Cl.

| | |
|---|---|
| ***A61K 31/519*** | (2006.01) |
| ***A61K 31/437*** | (2006.01) |
| ***A61K 31/496*** | (2006.01) |
| ***A61K 31/5377*** | (2006.01) |
| ***A61K 31/635*** | (2006.01) |
| ***A61K 31/675*** | (2006.01) |
| ***A61K 45/06*** | (2006.01) |
| ***A61P 35/00*** | (2006.01) |
| ***A61P 35/02*** | (2006.01) |

(52) U.S. Cl.
CPC .......... *A61K 31/519* (2013.01); *A61K 31/437* (2013.01); *A61K 31/5377* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 11,124,518 | B2 | 9/2021 | Huang et al. | |
| 11,251,192 | B2 | 2/2022 | Lee | |
| 11,261,192 | B2 * | 3/2022 | Huang ............... | C07D 491/048 |
| 12,410,204 | B2 | 9/2025 | Abraham et al. | |
| 12,606,567 | B2 | 4/2026 | Hopkins et al. | |
| 2014/0199234 | A1 | 7/2014 | Wang et al. | |
| 2015/0313907 | A1 | 11/2015 | Le Tiran et al. | |
| 2020/0157112 | A1 | 5/2020 | Huang et al. | |
| 2021/0139482 | A1 | 5/2021 | Huang et al. | |
| 2021/0317124 | A1 | 10/2021 | Huang et al. | |
| 2022/0024939 | A1 | 1/2022 | Huang et al. | |
| 2023/0002426 | A1 | 1/2023 | Huang et al. | |
| 2023/0008362 | A1 | 1/2023 | Samatar et al. | |
| 2023/0068370 | A1 | 3/2023 | Samatar et al. | |
| 2023/0087941 | A1 | 3/2023 | Samatar et al. | |
| 2023/0210854 | A1 | 7/2023 | Samatar et al. | |
| 2023/0234956 | A1 | 7/2023 | Huang et al. | |
| 2023/0265097 | A1 | 8/2023 | Hopkins et al. | |
| 2024/0197743 | A1 | 6/2024 | Pultar et al. | |
| 2024/0261295 | A1 | 8/2024 | Donate et al. | |
| 2024/0299395 | A1 | 9/2024 | Donate et al. | |
| 2024/0325397 | A1 | 10/2024 | Samatar et al. | |
| 2024/0325412 | A1 | 10/2024 | Donate et al. | |
| 2024/0335447 | A1 | 10/2024 | Donate et al. | |
| 2024/0391924 | A1 | 11/2024 | Huang et al. | |
| 2024/0408097 | A1 | 12/2024 | Samatar et al. | |
| 2025/0205240 | A1 | 6/2025 | Jameson et al. | |

(Continued)

FOREIGN PATENT DOCUMENTS

| | | |
|---|---|---|
| CN | 108601839 A | 9/2018 |
| WO | WO 2015/011400 | 1/2015 |

(Continued)

OTHER PUBLICATIONS

Golub et al., Science, vol. 286, Oct. 15, 1999, pp. 531-537 (Year: 1999).*
Jong et al., WEE1 Inhibition Enhances Anti-Apoptotic Dependency as a Result of Premature Mitotic Entry and DNA Damage, Cancers 2019, 11, 1743, Nov. 7, 2019 (Year: 2019).*
WO 2019037678-A1 Machine Translation (Year: 2019).*
Dancey et al., Strategies for optimizing combinations of molecularly targeted anticancer agents, Nature Reviews | Drug Discovery, vol. 5 | Aug. 2006 (Year: 2006).*
International Preliminary Report on Patentability issued May 17, 2022 for PCT Application No. PCT/US2020/065410, filed Dec. 16, 2020.
Office Action dated Sep. 30, 2024 for CN Application No. 202080095323.7, filed Dec. 16, 2020.
Examination Report dated Aug. 27, 2024 for NZ Patent Application No. 790037, filed Dec. 16, 2020.

(Continued)

*Primary Examiner* — Kortney L. Klinkel
*Assistant Examiner* — Alison Azar Hastings
(74) *Attorney, Agent, or Firm* — Knobbe, Martens, Olson & Bear, LLP

(57) ABSTRACT

Disclosed herein are combinations of compounds for treating a disease or condition, such as cancer. A combination of compounds for treating a disease or condition can include a Bcl-2 inhibitor and a WEE1 inhibitor, along with pharmaceutically acceptable salts of any of the foregoing.

12 Claims, 5 Drawing Sheets

(56) References Cited

U.S. PATENT DOCUMENTS

| | | | |
|---|---|---|---|
| 2025/0208149 | A1 | 6/2025 | Harismendy et al. |
| 2025/0262214 | A1 | 8/2025 | Ma et al. |
| 2025/0262215 | A1 | 8/2025 | Chung et al. |
| 2026/0028363 | A1 | 1/2026 | Abraham et al. |
| 2026/0083742 | A1 | 3/2026 | Ma et al. |

FOREIGN PATENT DOCUMENTS

| | | | |
|---|---|---|---|
| WO | WO 2017/079399 A1 | 5/2017 | |
| WO | WO 2018/027097 | 2/2018 | |
| WO | WO 2018/127130 | 7/2018 | |
| WO | WO 2018/154004 | 8/2018 | |
| WO | WO 2018/192462 | 10/2018 | |
| WO | WO 2019/028008 | 2/2019 | |
| WO | WO-2019037678 A1 * | 2/2019 | ........... A61K 31/519 |
| WO | WO 2019/139899 | 7/2019 | |
| WO | WO 2019/139900 | 7/2019 | |
| WO | WO 2019/139902 | 7/2019 | |
| WO | WO 2019/139907 | 7/2019 | |
| WO | WO-2019139899 A1 * | 7/2019 | ........... A61K 31/496 |
| WO | WO 2019/165204 | 8/2019 | |
| WO | WO 2019/169062 | 9/2019 | |
| WO | WO 2019/169065 | 9/2019 | |
| WO | WO 2019/173082 | 9/2019 | |
| WO | WO-2019173082 A1 * | 9/2019 | ........... A61K 31/519 |
| WO | WO 2019/210828 | 11/2019 | |
| WO | WO 2020/089286 | 5/2020 | |
| WO | WO 2020/210320 | 10/2020 | |
| WO | WO 2021/097139 | 5/2021 | |
| WO | WO 2021/127039 | 6/2021 | |
| WO | WO 2021/127044 | 6/2021 | |
| WO | WO 2021/127047 | 6/2021 | |
| WO | WO 2021/231653 | 11/2021 | |
| WO | WO 2021/252667 | 12/2021 | |
| WO | WO 2022/011391 | 1/2022 | |
| WO | WO 2022/136916 | 6/2022 | |
| WO | WO 2022/221143 | 10/2022 | |
| WO | WO 2022/251224 | 12/2022 | |
| WO | WO 2022/271731 | 12/2022 | |
| WO | WO 2023/064282 | 4/2023 | |
| WO | WO 2023/076485 | 5/2023 | |
| WO | WO 2023/114871 | 6/2023 | |
| WO | WO 2023/114875 | 6/2023 | |
| WO | WO 2023/114877 | 6/2023 | |
| WO | WO 2024/031048 | 2/2024 | |
| WO | WO 2024/059696 | 3/2024 | |
| WO | WO 2024/059808 | 3/2024 | |
| WO | WO 2024/102649 | 5/2024 | |
| WO | WO 2024/102650 | 5/2024 | |
| WO | WO 2024/249756 | 12/2024 | |
| WO | WO 2025/076311 | 4/2025 | |
| WO | WO 2025/106635 | 5/2025 | |
| WO | WO 2025/179038 | 8/2025 | |
| WO | WO 2025/184572 | 9/2025 | |
| WO | WO 2025/188946 | 9/2025 | |
| WO | WO 2025/193930 | 9/2025 | |
| WO | WO 2025/226653 | 10/2025 | |
| WO | WO 2025/231223 | 11/2025 | |
| WO | WO 2026/112362 | 5/2026 | |

OTHER PUBLICATIONS

Dejong et al., "WEE1 Inhibition Enhances Anti-Apoptotic Dependency as a Result of Premature Mitotic Entry and DNA Damage" Cancers (2019) 11:1743.

Lin et al., "Abstract 2497: FCN-338, a novel and selective Bcl-2 inhibitor, exhibits potent anti-tumor activity in B-cell lymphoma" Cancer Res. (2019) 79(Supplement 13):2497.

Scheffold et al., "Venetoclax: Targeting BCL2 in Hematological Cancers" Small Molecules in Hematology (2018):215-242.

Wilson et al., "Safety, Pharmacokinetics, Pharmacodynamics, and Activity of Navitoclax, a Targeted High Affinity Inhibitor of BCL-2, in Lymphoid Malignancies" Lancet Oncol. (2010) 11(12):1149-1159.

Office Action dated Jul. 4, 2024 for RU Application No. 2022118761, filed Dec. 16, 2020.

Office Action and Search Report dated May 28, 2024 for TW Application No. 109145167, filed Dec. 18, 2020.

Geenan et al., "Molecular Pathways: Targeting the Protein Kinase Wee1 in Cancer" Clincal Cancer Research (2017) 23(16):4540-4544.

International Search Report and Written Opinion mailed Feb. 3, 2021 for PCT Application No. PCT/US2020/065410, filed Dec. 16, 2020.

Brandwein et al., "BCL-2 Inhibitor Venetoclax Enhances Temozolomide Sensitivity in AML" Blood (2019) 143(Supplement 1):2646.

Ryan et al., "BCL-2 Inhibitors, Present and Future" Cancer Journal (2019) 25(6):401-409.

Extended European Search Report dated Dec. 11, 2023 for EP Application No. 20904098.9, filed Dec. 16, 2020.

Tabayashi et al., "Inhibition of WEE1 Induces Cell Death of Both Bortezomib- and Lenalidomide-Resistant Multiple Myeloma Cells: A Novel Therapeutic Approach Targeting Cell-Cycle Checkpoint Kinase" Blood (2016) 128(22):3256.

Office Action dated Apr. 9, 2025 for CN Application No. 202080095323.7, filed Dec. 16, 2020.

Office Action dated Apr. 9, 2025 for IL Application No. 294094, filed Dec. 16, 2020.

First Examination Report dated Jun. 13, 2025 for IN Application No. 202217041350, filed Dec. 16, 2020.

Office Action dated Dec. 5, 2024 for JP Application No. 2022-538232, filed Dec. 16, 2020.

Examination Report dated Mar. 4, 2025 for NZ Patent Application No. 790037, filed Dec. 16, 2020.

Examination Report dated May 14, 2025 for NZ Patent Application No. 790037, filed Dec. 16, 2020.

Examination Report dated May 27, 2025 for NZ Patent Application No. 790037, filed Dec. 16, 2020.

Office Action dated Nov. 8, 2024 for RU Application No. 2022118761, filed Dec. 16, 2020.

Office Action dated Jun. 20, 2025 for CN Application No. 202080095323.7, filed Dec. 16, 2020.

Examination Report dated Sep. 24, 2025 for AU Application No. 2020404996, filed Dec. 16, 2020.

Search Report dated Nov. 28, 2025 for BR Application No. BR112022012283-7, filed Dec. 16, 2020.

Office Action dated Dec. 19, 2025 for CA Application No. 3,165,474, filed Dec. 16, 2020.

Office Action dated Feb. 20, 2026 for KR Application No. 10-2022-7024701, filed Dec. 16, 2020.

Office Action dated Oct. 14, 2025 for MX Application No. MX/a/2022/007623, Dec. 16, 2020.

* cited by examiner

| Compound No. | Structure |
| --- | --- |
| 1 | AGP-2575 |
| 2 | AGP-1252 |
| 3 |  venetoclax (ABT-199) |
| 4 |  navitoclax (ABT-263) |
| 5 |  (S55746/BCL201) |
| 6 | S65487 |
| 7 | BGB-11417 |
| 8 | FCN-338 |
| 9 | AZD0466 |

| Compound No. | Structure |
|---|---|
| 1A |  |
| 2A |  |
| 3A |  |
| 4A |  |
| 5A |  |
| 6A |  |

| Compound No. | Structure |
|---|---|
| 7A |  |
| 8A |  |
| 9A |  |
| 10A |  |
| 11A |  |
| 12A |  |

COMBINATIONS OF WEE1 INHIBITORS AND Bcl-2 INHIBITORS FOR TREATMENT OF CANCER

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/952,032, filed Dec. 20, 2019.

FIELD

The present application relates to the fields of chemistry, biochemistry and medicine. More particularly, disclosed herein are combination therapies, and methods of treating diseases and/or conditions with a combination therapies descried herein.

DESCRIPTION

Cancers are a family of diseases that involve abnormal cell growth with the potential to invade or spread to other parts of the body. Cancer treatments today include surgery, hormone therapy, radiation, chemotherapy, immunotherapy, targeted therapy and combinations thereof. Survival rates vary by cancer type and by the stage at which the cancer is diagnosed. In 2019, roughly 1.8 million people will be diagnosed with cancer, and an estimated 606,880 people will die of cancer in the United States. Thus, there still exists a need for effective cancer treatments.

SUMMARY

Some embodiments described herein relate to a combination of compounds that can include an effective amount of Compound (A), or a pharmaceutically acceptable salt thereof, and an effective amount of one or more of Compound (B), or a pharmaceutically acceptable salt thereof.

Some embodiments described herein relate to the use of a combination of compounds for treating a disease or condition, wherein the combination includes an effective amount of Compound (A), or a pharmaceutically acceptable salt thereof, and an effective amount of one or more of Compound (B), or a pharmaceutically acceptable salt thereof. Other embodiments described herein relate to the use of a combination of compounds in the manufacture of a medicament for treating a disease or condition, wherein the combination includes an effective amount of Compound (A), or a pharmaceutically acceptable salt thereof, and an effective amount of one or more of Compound (B), or a pharmaceutically acceptable salt thereof.

In some embodiments, the disease or condition can be a cancer described herein.

DRAWINGS

FIG. 1 provides examples of Bcl-2 inhibitors.

FIG. 2 provides examples of Compound (A).

DETAILED DESCRIPTION

Definitions

Figure 1:
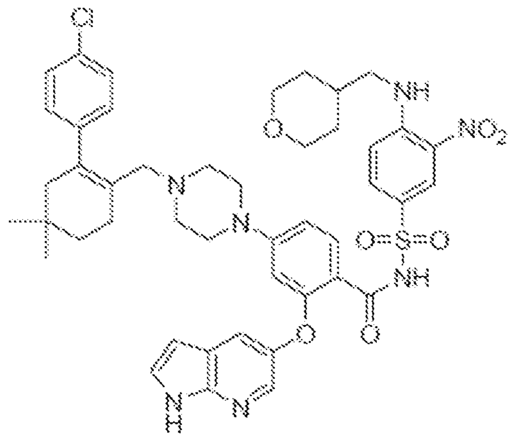
Figure 1:
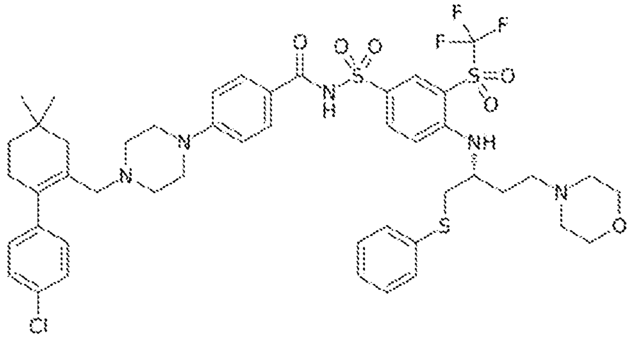
Figure 1:
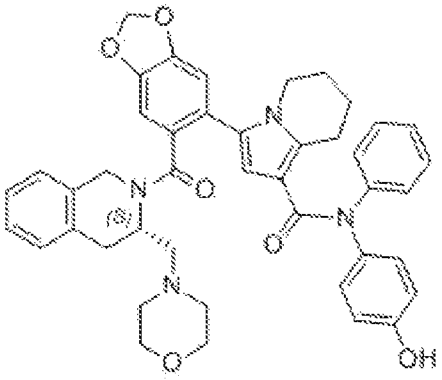

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, hydroxyalkyl, haloalkoxy, an amino, a mono-substituted amine group, a di-substituted amine group and an amine ($C_1$-$C_6$ alkyl).

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

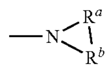

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms"

means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups and cycloalkenyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

As used herein, "lower alkylene groups" are straight-chained $—CH_2$-tethering groups, forming bonds to connect molecular fragments via their terminal carbon atoms. Examples include but are not limited to methylene $(—CH_2—)$, ethylene $(—CH_2CH_2—)$, propylene $(—CH_2CH_2CH_2—)$ and butylene $(—CH_2CH_2CH_2CH_2—)$. A lower alkylene group can be substituted by replacing one or more hydrogen of the lower alkylene group and/or by substituting both hydrogens on the same carbon with a cycloalkyl group (e.g., 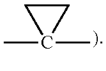).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (iso-propoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "$—OC(=O)N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "$ROC(=O)N(R_A)—$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "$—OC(=S)—N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "$ROC(=S)N(R_A)—$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "$—C(=O)N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "$RC(=O)N(R_A)—$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "$—SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(═O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(═O)OR" group in which R can be the same as defined with respect to O-carboxy. An ester and C-carboxy may be substituted or unsubstituted.

A "nitro" group refers to an "—$NO_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —$NH_2$ group.

A "mono-substituted amine" group refers to a "—$NHR_A$" group in which $R_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The $R_A$ may be substituted or unsubstituted. Examples of mono-substituted amino groups include, but are not limited to, —NH(methyl), —NH(phenyl) and the like.

A "di-substituted amine" group refers to a "—$NR_AR_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. Examples of di-substituted amino groups include, but are not limited to, —N(methyl)$_2$, —N(phenyl)(methyl), —N(ethyl)(methyl) and the like.

As used herein, "amine(alkyl)" group refers to an -(alkylene)-NR'R" radical where R' and R" are independently hydrogen or alkyl as defined herein. An amine(alkyl) may be substituted or unsubstituted. Examples of amine(alkyl) groups include, but are not limited to, —$CH_2$NH(methyl), —$CH_2$NH(phenyl), —$CH_2CH_2$NH(methyl), —$CH_2CH_2$NH(phenyl), —$CH_2$N(methyl)$_2$, —$CH_2$N(phenyl)(methyl), —$NCH_2$(ethyl)(methyl), —$CH_2CH_2$N(methyl)$_2$, —$CH_2CH_2$N(phenyl)(methyl), —$NCH_2CH_2$(ethyl)(methyl) and the like.

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine and salts with amino acids such as arginine and lysine. Those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to the use of a combination of compounds for treating a disease or condition, wherein the combination can include an effective amount of Compound (A), or a pharmaceutically acceptable salt thereof, and an effective amount of one or more of Compound (B), or a pharmaceutically acceptable salt thereof, wherein: the Compound (A) has the structure:

(A)

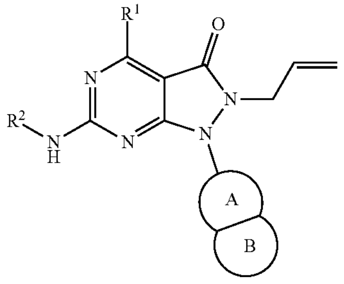

wherein: $R^1$ can be selected from hydrogen, halogen and a substituted or unsubstituted $C_1$-$C_6$ alkyl; Ring A can be selected from a substituted or unsubstituted phenyl and a substituted or unsubstituted 5-6 membered monocyclic heteroaryl; Ring B can be selected from a substituted or unsubstituted monocyclic 5-7 membered carbocyclyl and a substituted or unsubstituted 5-7 membered monocyclic heterocyclyl; $R^2$ can be selected from

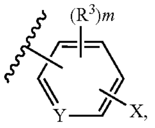

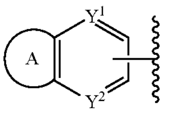

and

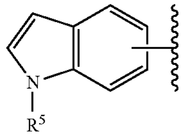

;

m can be 0, 1, 2 or 3; $R^3$ can be selected from halogen and a substituted or unsubstituted $C_1$-$C_6$ alkyl; X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl; Y can be CH or N; $Y^1$ can be $CR^{4A}$ or N; $Y^2$ can be $CR^{4B}$ or N; Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl; $R^{4A}$ and $R^{4B}$ can be independently selected from hydrogen, halogen and an unsubstituted $C_{1-4}$ alkyl; and $R^5$ can be a substituted or unsubstituted 5-7 membered monocyclic heterocyclyl; and the one or more of Compound (B) can be a Bcl-2 inhibitor, or a pharmaceutically acceptable salt thereof.

In some embodiments, $R^1$ can be selected from hydrogen, halogen and a substituted or unsubstituted $C_1$-$C_6$ alkyl. In some embodiments, Ring A can be selected from a substituted or unsubstituted phenyl and a substituted or unsubstituted 5-6 membered monocyclic heteroaryl. In some embodiments, Ring B can be selected from a substituted or unsubstituted monocyclic 5-7 membered carbocyclyl and a substituted or unsubstituted 5-7 membered monocyclic heterocyclyl. In some embodiments, $R^2$ can be selected from

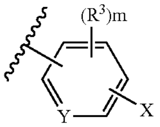
and
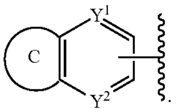
.

In some embodiments, m can be 0, 1, 2 or 3. In some embodiments, $R^3$ can be selected from halogen and a substituted or unsubstituted $C_1$-$C_6$ alkyl. In some embodiments, X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl, a substituted or unsubstituted $C_1$-$C_6$ alkoxy, a substituted or unsubstituted $C_3$-$C_6$ cycloalkoxy, a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl. In some embodiments, Y can be CH or N. In some embodiments, $Y^1$ can be $CR^{4A}$ or N. In some embodiments, $Y^2$ can be $CR^{4B}$ or N. In some embodiments, Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl. In some embodiments, $R^{4A}$ and $R^{4B}$ are independently selected from hydrogen, halogen and an unsubstituted $C_{1-4}$ alkyl.

In some embodiments, $R^1$ can be selected from hydrogen, halogen and $C_1$-$C_6$ alkyl. In some embodiments, $R^1$ can be hydrogen. In other embodiments, $R^1$ can be halogen. In some embodiments, $R^1$ can be fluoro. In still other embodiments, $R^1$ can be an unsubstituted $C_1$-$C_6$ alkyl (such as methyl, ethyl, n-propyl, iso-propyl, n-butyl, iso-butyl, sec-butyl, t-butyl, pentyl (straight chain or branched) or hexyl (straight chain or branched)). In some embodiments, $R^1$ can be an unsubstituted methyl. In some embodiments, $R^1$ can be a substituted $C_1$-$C_6$ alkyl, such as those described herein. In some embodiments, $R^1$ can be an unsubstituted $C_1$-$C_6$ haloalkyl (such as a $C_1$-$C_6$ fluoroalkyl, a $C_1$-$C_6$ chloroalkyl or a $C_1$-$C_6$ chlorofluoroalkyl). In some embodiments, $R^1$ can be —$CHF_2$, —$CF_3$, —$CF_2CH_3$ or —$CH_2CF_3$.

In some embodiments, Ring A can be selected from a substituted or unsubstituted phenyl and a substituted or unsubstituted 5-6 membered monocyclic heteroaryl.

In some embodiments, Ring A can be a substituted phenyl. In other embodiments, Ring A can be an unsubstituted phenyl.

In some embodiments, Ring A can be a substituted 5-6 membered monocyclic heteroaryl. In some embodiments, Ring A can be an unsubstituted 5-6 membered monocyclic heteroaryl. In some embodiments, Ring A can be selected from a substituted or unsubstituted pyrrole, a substituted or unsubstituted furan, a substituted or unsubstituted thiophene, a substituted or unsubstituted imidazole, a substituted or unsubstituted pyrazole, a substituted or unsubstituted oxazole, a substituted or unsubstituted thiazole, a substituted or unsubstituted pyridine, a substituted or unsubstituted pyrazine, a substituted or unsubstituted pyrimidine and a substituted or unsubstituted pyridazine.

When substituted, Ring A can be substituted with one or more substituents selected from halogen, an unsubstituted $C_1$-$C_4$ haloalkyl and an unsubstituted $C_1$-$C_4$ alkyl. In some embodiments, Ring A is mono-substituted with a halogen (for example, fluoro).

In some embodiments,

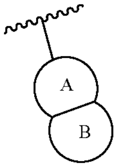

can be selected from:

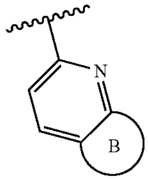
,
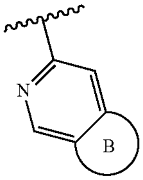
,
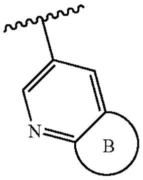
,
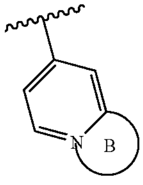
,
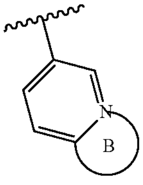
,
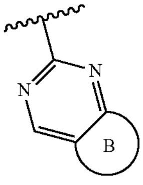
,
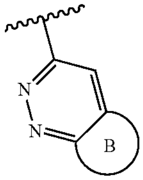
,
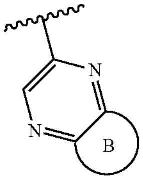
,
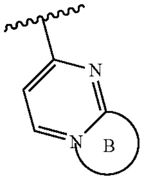
, -continued

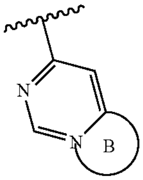, 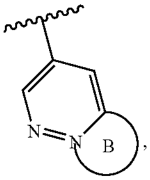, 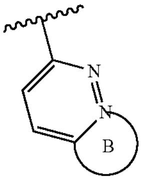,

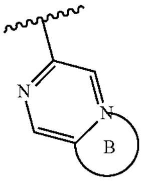, 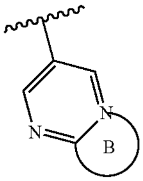, 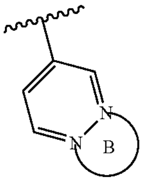,

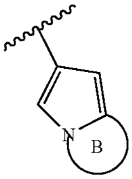, 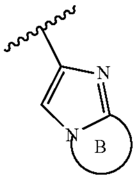, 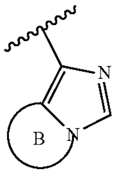,

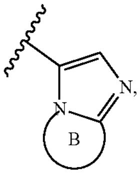 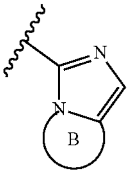, 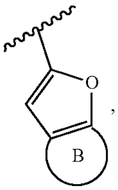,

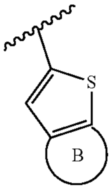 and 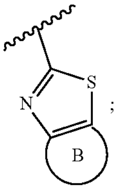;

wherein each of the aforementioned groups are substituted or unsubstituted. In some embodiments,

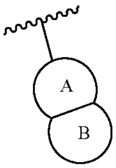

can be a substituted or unsubstituted

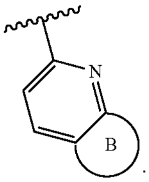.

In some embodiments,

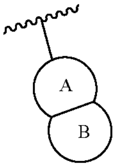

can be a substituted or unsubstituted

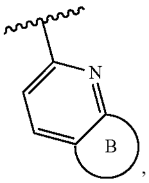, wherein the Ring A is unsubstituted. In other embodiments,

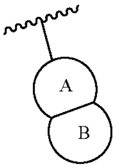

can be selected from a substituted or unsubstituted

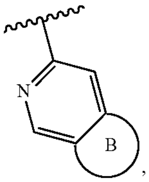, a substituted or unsubstituted

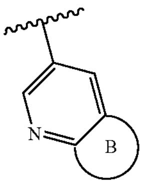

and a substituted or unsubstituted

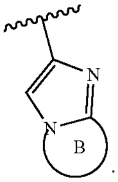.

As described herein, the Ring A portion of

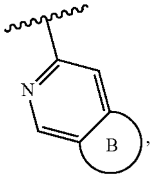, a 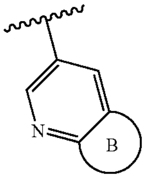 and 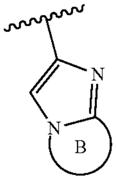

can be unsubstituted.

In some embodiments, Ring B can be selected from a substituted or unsubstituted monocyclic 5-7 membered carbocyclyl and a substituted or unsubstituted 5-7 membered monocyclic heterocyclyl.

In some embodiments, Ring B can be a substituted or unsubstituted monocyclic 5-7 membered carbocyclyl. In some embodiments, Ring B can be a substituted or unsubstituted monocyclic 5 membered carbocyclyl. In other embodiments, Ring B can be a substituted or unsubstituted monocyclic 6 membered carbocyclyl. In still other embodiments, Ring B can be a substituted or unsubstituted monocyclic 7 membered carbocyclyl.

In some embodiments,

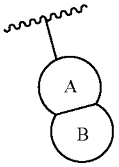

can be selected from:

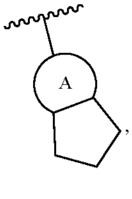, 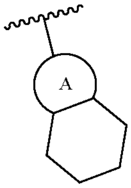 and 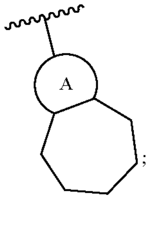;

wherein each of the aforementioned groups are substituted or unsubstituted.

In some embodiments, Ring B can be a substituted or unsubstituted monocyclic 5-7 membered heterocyclyl. In some embodiments, Ring B can be a substituted or unsubstituted monocyclic 5 membered heterocyclyl. In other embodiments, Ring B can be a substituted or unsubstituted monocyclic 6 membered heterocyclyl. In still other embodiments, Ring B can be a substituted or unsubstituted monocyclic 7 membered heterocyclyl.

In some embodiments,

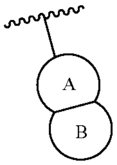

can be selected from:

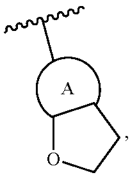, 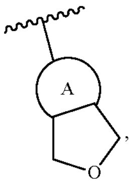, 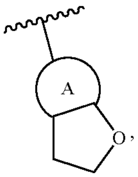, 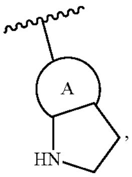,

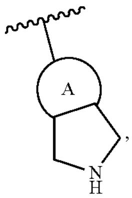, 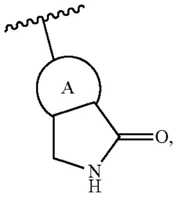, 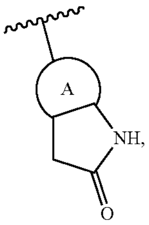

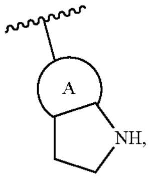, 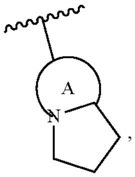, 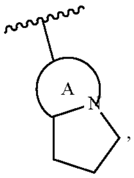,

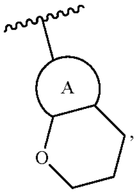, 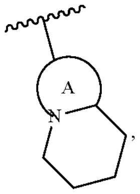, 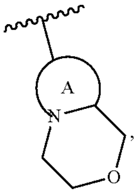, 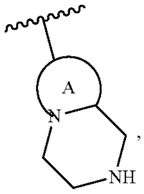,

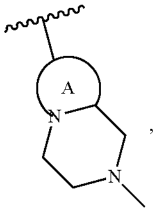, 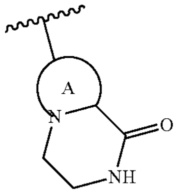 and

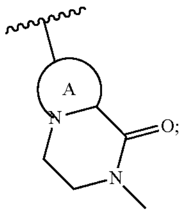

wherein each of the aforementioned groups are substituted or unsubstituted, including any —NH group.

In some embodiments, Ring B can be selected from

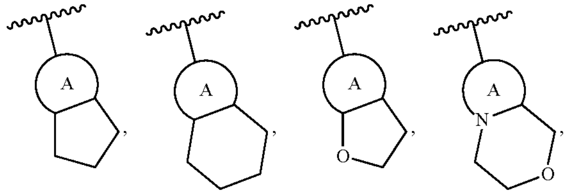

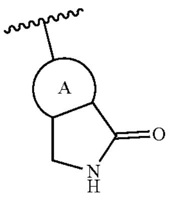 and 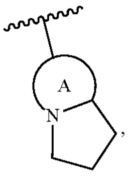

wherein each of the aforementioned groups are substituted or unsubstituted, including any —NH group. In some embodiments, Ring B can be a substituted or unsubstituted

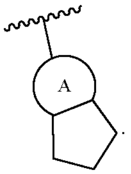

In some embodiments, when Ring B is substituted, Ring B can be substituted with 1, 2 or 3 substituents independently selected from halogen, hydroxy, amino, an unsubstituted N-linked amido (for example, —NHC(O)$C_1$-$C_6$ alkyl), an unsubstituted $C_1$-$C_6$ haloalkyl (such as those described herein) and a substituted or unsubstituted $C_1$-$C_6$ alkyl (such as those described herein). In some embodiments, when Ring B is substituted, Ring B can be substituted with 1, 2 or 3 substituents independently selected from halogen, hydroxy, amino, an unsubstituted N-linked amido (for example, —NHC(O)$C_1$-$C_6$ alkyl) and a substituted or unsubstituted $C_1$-$C_6$ alkyl (such as those described herein). In some embodiments, Ring B can be substituted with 1, 2 or 3 substituents independently selected from fluoro, hydroxy, amino, an unsubstituted —NHC(O)$C_1$-$C_6$ alkyl, an unsubstituted $C_1$-$C_6$ haloalkyl (such as those described herein) and an unsubstituted $C_1$-$C_6$ alkyl (such as those described herein). In some embodiments, Ring B can be substituted with 1 or 2 substituents independently selected from fluoro, hydroxy, —$CF_3$, —$CHF_2$, —$CF_2CH_3$, an unsubstituted methyl, an unsubstituted ethyl and —NHC(O)$CH_3$.

In some embodiments,

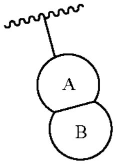

can be selected from:

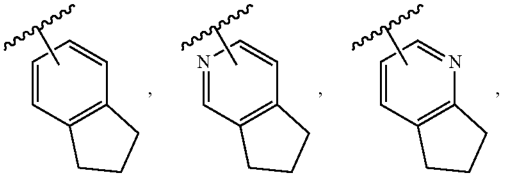

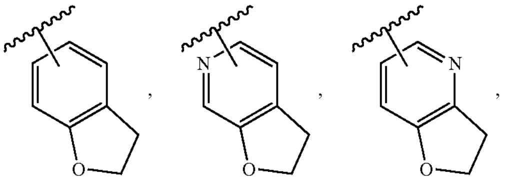

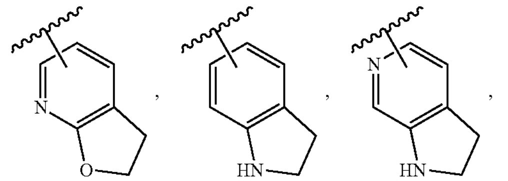

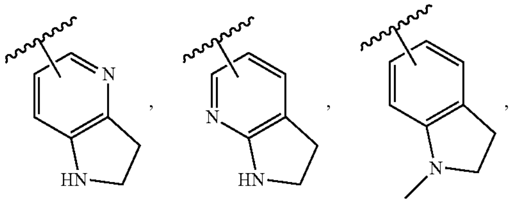

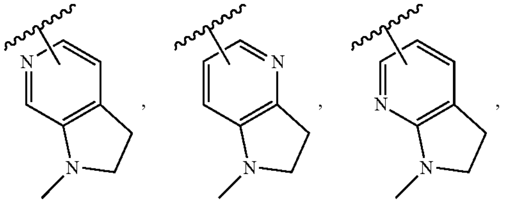

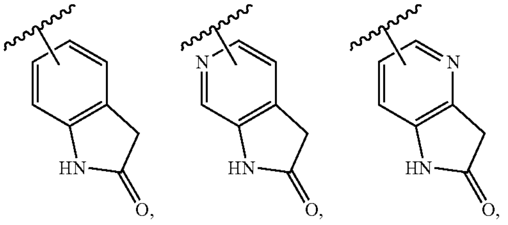

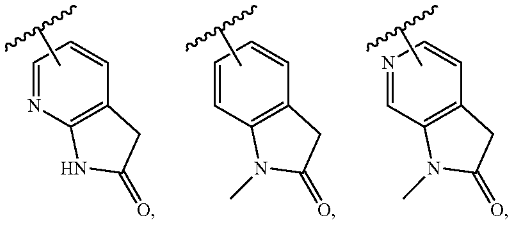

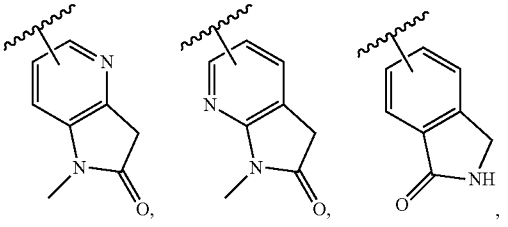

-continued
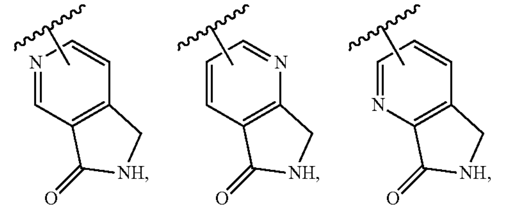
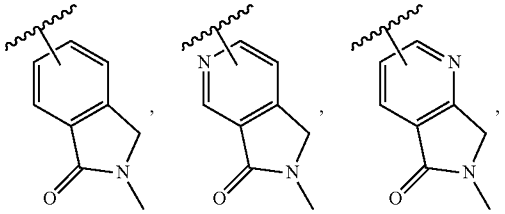
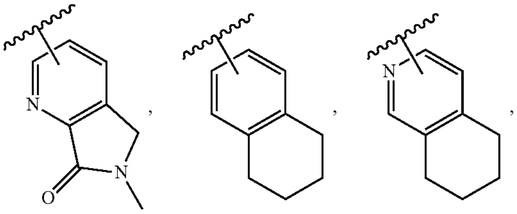
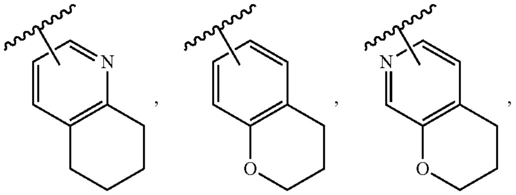
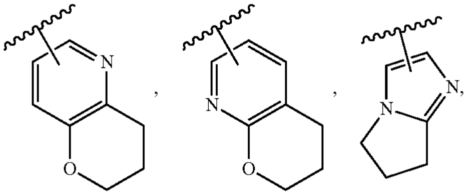
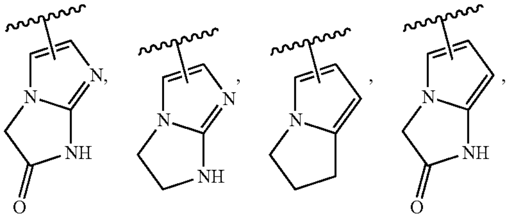
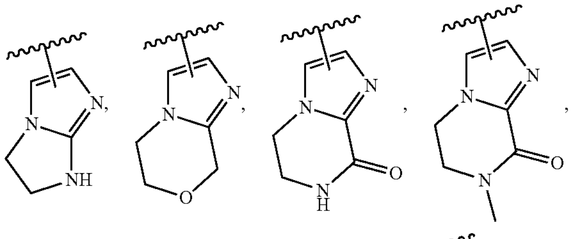
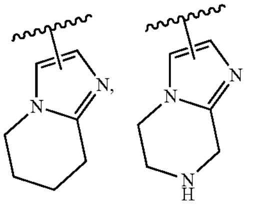
and
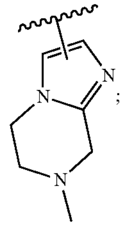
wherein each of the aforementioned groups are substituted or unsubstituted, including any —NH group.
In some embodiments,
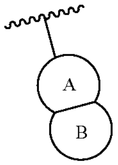
can be selected from:
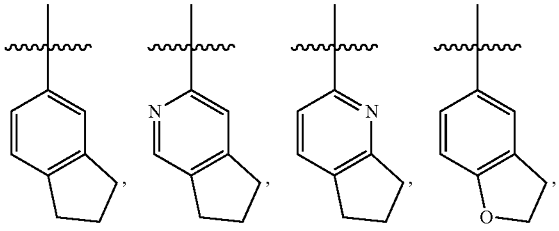
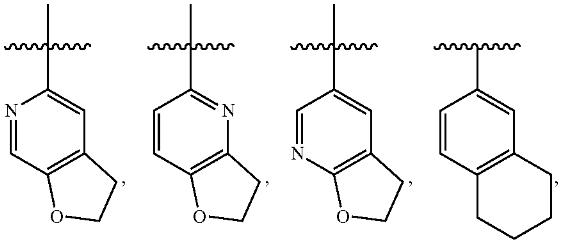
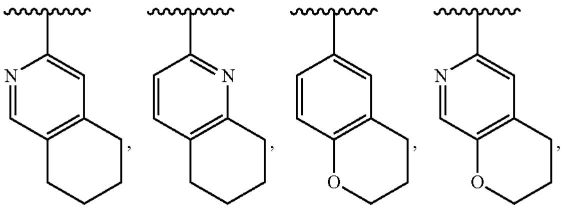
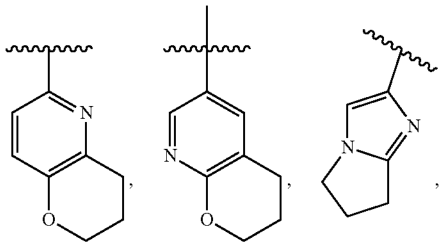
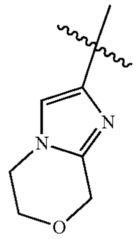
and
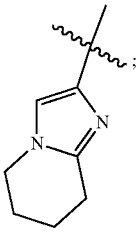

wherein each of the aforementioned groups are substituted or unsubstituted. In some embodiments,

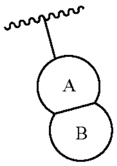

can be selected from:

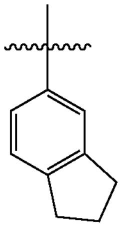, 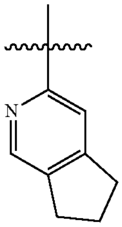, 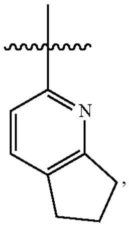, 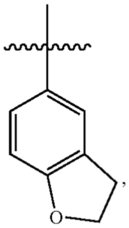, 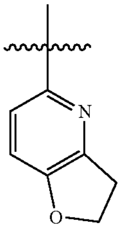, 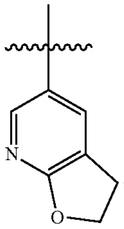, 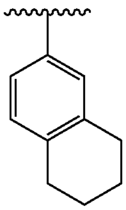, 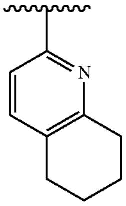, 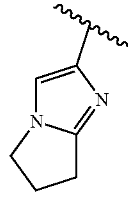 and 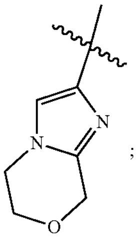;

wherein each of the aforementioned groups are substituted or unsubstituted. In some embodiments,

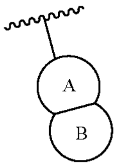

can be a substituted or unsubstituted

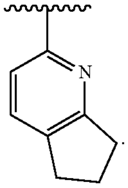 [SMILES: *c1ccc2c(n1)CCC2].

In some embodiments,

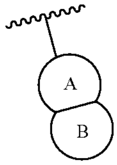

can be a substituted or

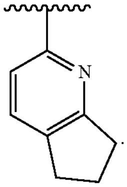 [SMILES: *c1ccc2c(n1)CCC2].

Both Ring A and Ring B can be substituted or unsubstituted. In some embodiments, Ring A and Ring B of

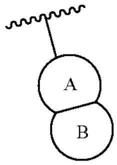

can be independently substituted or unsubstituted. In some embodiments, Ring A and Ring B of

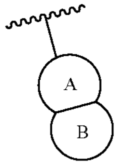

can be both unsubstituted. In some embodiments, Ring A and Ring B of

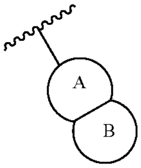

can be both independently substituted. In some embodiments, Ring A of

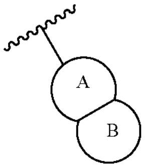

can be substituted and Ring B of

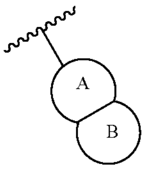

can be unsubstituted. In some embodiments, Ring A of

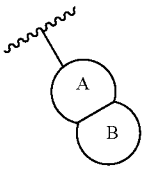

can be unsubstituted and Ring B of

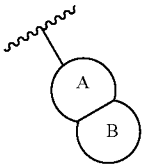

can be substituted. In some embodiments, Ring A of

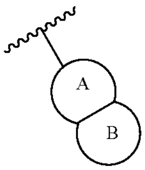

can be unsubstituted and Ring B of

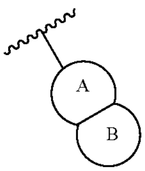

can be substituted with 1, 2 or 3 substituents independently selected from halogen, hydroxy and a substituted or unsubstituted $C_1$-$C_6$ alkyl (such as those described herein). In some embodiments, Ring A of

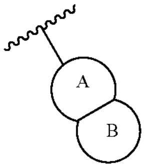

can be unsubstituted and Ring B of

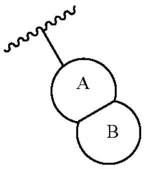

can be substituted with 1, 2 or 3 substituents independently selected from fluoro, hydroxy, amino, an unsubstituted N-linked amido (for example, —NHC(O)$C_1$-$C_6$ alkyl), an unsubstituted $C_1$-$C_6$ haloalkyl (such as those described herein) and an unsubstituted $C_1$-$C_6$ alkyl (such as those described herein). In some embodiments, Ring A of

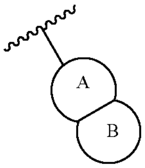

can be unsubstituted and Ring B of

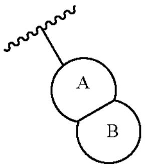

can be substituted with 1 or 2 substituents independently selected from fluoro, hydroxy, amino, —$CF_3$, —$CHF_2$, —$CF_2CH_3$, an unsubstituted methyl, an unsubstituted ethyl and —NHC(O)$CH_3$.

In some embodiments, $R^2$ can be selected from

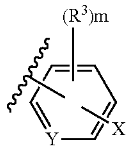

and

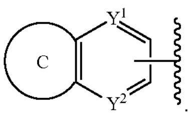

.

In some embodiments, $R^2$ can be

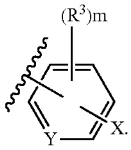

In some embodiments, $R^2$ can be

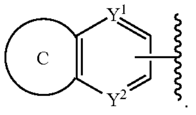

In some embodiments, Y can be CH or N (nitrogen). In some embodiments, Y can be CH. In some embodiments, Y can be N (nitrogen).

In some embodiments, $R^3$ can be selected from halogen and a substituted or unsubstituted $C_1$-$C_6$ alkyl (such as those described herein). In some embodiments, $R^3$ can be halogen. In some embodiments, $R^3$ can be a substituted $C_1$-$C_6$ alkyl (such as those described herein). In some embodiments, $R^3$ can be an unsubstituted $C_1$-$C_6$ alkyl (such as those described herein).

In some embodiments, m can be 0, 1, 2 or 3. In some embodiments, m can be 0. In some embodiments, m can be 1. In some embodiments, m can be 2. In some embodiments, m can be 3. When m is 2 or 3, the $R^3$ groups can be the same or different from each other.

In some embodiments, X can be selected from hydrogen, halogen, hydroxy, cyano, a substituted or unsubstituted 4-6 membered monocyclic heterocyclyl, a substituted or unsubstituted amine($C_1$-$C_6$ alkyl), a substituted or unsubstituted —NH—$(CH_2)_{1-6}$-amine, a mono-substituted amine, a di-substituted amine, an amino, a substituted or unsubstituted $C_1$-$C_6$ alkyl (such as those described herein), a substituted or unsubstituted $C_1$-$C_6$ alkoxy (such as methoxy, ethoxy, n-propoxy, iso-propoxy, n-butoxy, iso-butoxy, sec-butoxy, t-butoxy, pentoxy (straight chain or branched) or hexoxy (straight chain or branched)), a substituted or unsubstituted $C_3$-$C_6$ cycloalkoxy (such as cyclopropoxy, cyclobutoxy, cyclopentoxy or cyclohexoxy), a substituted or unsubstituted ($C_1$-$C_6$ alkyl)acyl, a substituted or unsubstituted C-amido, a substituted or unsubstituted N-amido, a substituted or unsubstituted C-carboxy, a substituted or unsubstituted O-carboxy, a substituted or unsubstituted O-carbamyl and a substituted or unsubstituted N-carbamyl.

In some embodiments, X can be hydrogen. In other embodiments, X can be halogen. In some embodiments, X can be fluoro. In some embodiments, X can be chloro. In still other embodiments, X can be hydroxy. In yet still other embodiments, X can be cyano. In some embodiments, X can be an amino.

In some embodiments, X can be an unsubstituted $C_1$-$C_6$ alkyl (such as those described herein). In some embodiments, X can be an unsubstituted methyl, an unsubstituted ethyl or an unsubstituted iso-propyl. In some embodiments, X can be a substituted $C_1$-$C_6$ alkyl (such as those described herein). In some embodiments, X can be an unsubstituted $C_1$-$C_6$ haloalkyl (such as a $C_1$-$C_6$ fluoroalkyl, a $C_1$-$C_6$ chloroalkyl or a $C_1$-$C_6$ chlorofluoroalkyl). In some embodiments, X can be selected from —$CHF_2$, —$CF_3$, —$CF_2CH_3$ and —$CH_2CF_3$. In some embodiments, X can be an unsubstituted $C_1$-$C_6$ hydroxyalkyl (such as a $C_1$-$C_6$ mono-hydroxyalkyl or a $C_1$-$C_6$ di-hydroxyalkyl). In some embodiments, X can be selected from —$CH_2OH$, —$CH_2CH_2OH$, —$CH(OH)CH_3$ and —$C(OH)(CH_3)_2$. In some embodiments, X can be an unsubstituted $C_1$-$C_6$ cyanoalkyl (such as a $C_1$-$C_6$ mono-cyanoalkyl or a $C_1$-$C_6$ di-cyanoalkyl). In some embodiments, X can be selected from

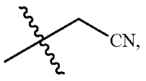 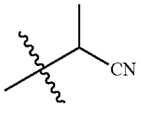 and 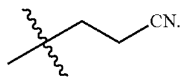

In some embodiments, X can be an unsubstituted $C_1$-$C_6$ alkoxyalkyl (such as a $C_1$-$C_6$ mono-alkoxyalkyl or a $C_1$-$C_6$ di-alkoxyalkyl). In some embodiments, X can be selected from

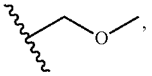 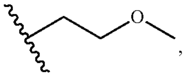

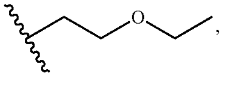 and 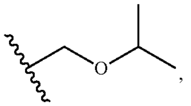

In some embodiments, X can be a substituted $C_1$-$C_6$ alkyl selected from

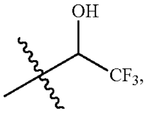 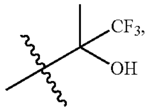 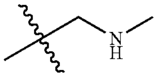 and

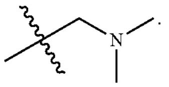

In some embodiments, X can be an unsubstituted $C_1$-$C_6$ alkoxy (such as those described herein). In some embodiments, X can be an unsubstituted methoxy, an unsubstituted ethoxy or an unsubstituted iso-propoxy. In some embodiments, X can be a substituted $C_1$-$C_6$ alkoxy (such as those described herein). In some embodiments, X can be a $C_1$-$C_6$ alkoxy substituted with 1, 2 or 3 substituents independently selected from halogen, an amino, a mono-substituted amine (such as those described herein) and a di-substituted amine (such as those described herein). In some embodiments, X can be a $C_1$-$C_6$ alkoxy substituted with 1 substituent selected from halogen, an amino, a mono-substituted amine (such as those described herein) and a di-substituted amine (such as those described herein).

In some embodiments, X can be selected from

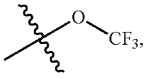 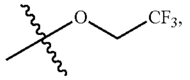 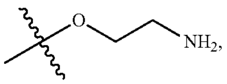

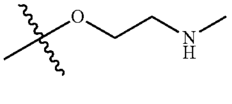 and 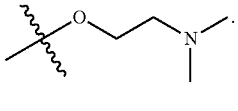

In some embodiments, X can be a substituted $C_3$-$C_6$ cycloalkoxy (such as those described herein). In some embodiments, X can be an unsubstituted $C_3$-$C_6$ cycloalkoxy (such as those described herein).

In some embodiments, X can be a substituted ($C_1$-$C_6$ alkyl)acyl, such as a substituted —(CO)—$CH_3$. In some embodiments, X can be an unsubstituted ($C_1$-$C_6$ alkyl)acyl, such as an unsubstituted —(CO)—$CH_3$.

In some embodiments, X can be a substituted 4-6 membered monocyclic heterocyclyl. In some embodiments, X can be an unsubstituted 4-6 membered monocyclic heterocyclyl. In some embodiments, X can be selected from azetidine, oxetane, diazetidine, azaoxetane, pyrrolidine, tetrahydrofuran, imidazoline, pyrazolidine, piperidine, tetrahydropyran, piperazine, morpholine and dioxane; wherein each of the aforementioned groups are substituted or unsubstituted, including any —NH group. . In some embodiments, X can be selected from

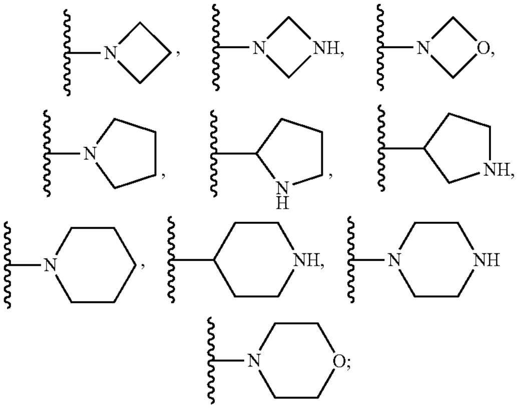

and wherein each of the aforementioned groups are substituted or unsubstituted, including any —NH group.

In some embodiments, X can be a 4-6 membered monocyclic heterocyclyl (such as those described herein) substituted with 1 or 2 substituents independently selected from halogen, a substituted or unsubstituted $C_1$-$C_6$ alkyl (such as those described herein), a mono-substituted amine (such as those described herein), a di-substituted amine (such as those described herein), an amino, substituted or unsubstituted amine($C_1$-$C_6$ alkyl) and a substituted or unsubstituted ($C_1$-$C_6$ alkyl)acyl. In some embodiments, X can be a 4-6 membered monocyclic heterocyclyl substituted with 1 or 2 substituents independently selected from fluoro, an unsubstituted methyl, an unsubstituted ethyl, an unsubstituted iso-propyl, —$CH_2OH$ and —$N(CH_3)_2$. In some embodiments, X can be selected from

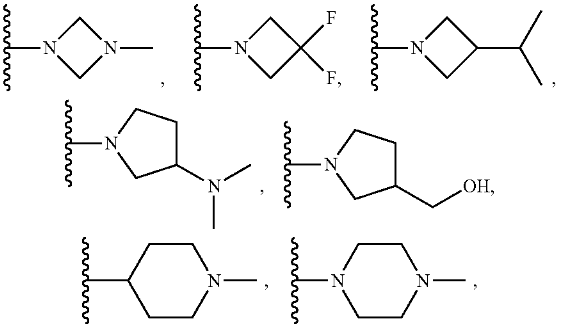

-continued

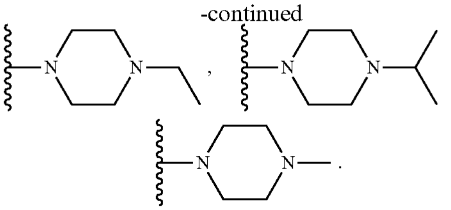

and

In some embodiments, X can be a substituted amine($C_1$-$C_6$ alkyl). In some embodiments, X can be an unsubstituted amine($C_1$-$C_6$ alkyl). In some embodiments, X can be selected from

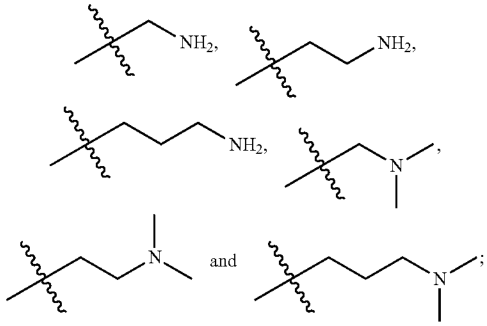

wherein each of the aforementioned groups are substituted or unsubstituted, including any —NH group.

In some embodiments, X can be a substituted —NH—$(CH_2)_{1-6}$-amine. In some embodiments, X can be an unsubstituted —NH—$(CH_2)_{1-6}$-amine. In some embodiments, X can be selected from

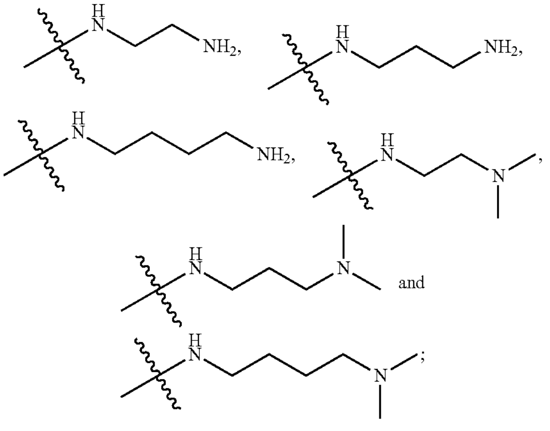

wherein each of the aforementioned groups are substituted or unsubstituted, including any —NH group.

In some embodiments, X can be a mono-substituted amine. In some embodiments, the substituent of the mono-substituted amine is an unsubstituted $C_1$-$C_6$ alkyl (such as those as described herein) or an unsubstituted $C_3$-$C_6$ cycloalkyl (such as cyclopropyl, cyclobutyl, cyclopentyl and cyclohexyl).

In some embodiments, X can be a di-substituted amine. In some embodiments, the two substituents of the di-substituted amine are independently selected from an unsubstituted $C_1$-$C_6$ alkyl (such as those as described herein) and an unsubstituted $C_3$-$C_6$ cycloalkyl (such as those as described herein).

In some embodiments, X can be selected from

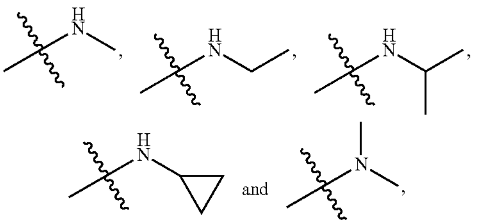

and

In some embodiments, X can be a substituted or unsubstituted C-amido. In some embodiments, X can be a substituted or unsubstituted N-amido. In some embodiments, X can be a substituted or unsubstituted C-carboxy. In some embodiments, X can be a substituted or unsubstituted O-carboxy. In some embodiments, X can be a substituted or unsubstituted O-carbamyl. In some embodiments, X can be a substituted or unsubstituted N-carbamyl. In some embodiments, X can be mono-substituted with an unsubstituted $C_1$-$C_6$ hydroxyalkyl (such as those described herein).

In some embodiments, $Y^1$ can be $CR^{4A}$ or N (nitrogen). In some embodiments, $Y^1$ can be $CR^{4A}$. In some embodiments, $Y^1$ can be N (nitrogen).

In some embodiments, $Y^2$ can be $CR^{4B}$ or N (nitrogen). In some embodiments, $Y^2$ can be $CR^{4B}$. In some embodiments, $Y^2$ can be N (nitrogen).

In some embodiments, $Y^1$ and $Y^2$ can each be N (nitrogen). In some embodiments, $Y^1$ can be $CR^{4A}$ and $Y^2$ can be $CR^{4B}$. In some embodiments, $Y^1$ can be $CR^{4A}$ and $Y^2$ can be N (nitrogen). In some embodiments, $Y^1$ can be N (nitrogen) and $Y^2$ can be $CR^{4B}$.

In some embodiments, $R^{4A}$ can be hydrogen. In some embodiments, $R^{4A}$ can be halogen. In some embodiments, $R^{4A}$ can be an unsubstituted $C_{1-4}$ alkyl (such as those described herein).

In some embodiments, $R^{4B}$ can be hydrogen. In some embodiments, $R^{4B}$ can be halogen. In some embodiments, $R^{4B}$ can be an unsubstituted $C_{1-4}$ alkyl (such as those described herein).

In some embodiments, $R^{4A}$ and $R^{4B}$ can each be hydrogen. In some embodiments, $R^{4A}$ and $R^{4B}$ can each be halogen (wherein the halogens can be the same or different from each other). In some embodiments, $R^{4A}$ and $R^{4B}$ can each be an unsubstituted $C_{1-4}$ alkyl (such as those described herein, and wherein the $C_{1-4}$ alkyls can be the same or different from each other). In some embodiments, one of $R^{4A}$ and $R^{4B}$ can be hydrogen and the other of $R^{4A}$ and $R^{4B}$ can be halogen. In some embodiments, one of $R^{4A}$ and $R^{4B}$ can be hydrogen and the other of $R^{4A}$ and $R^{4B}$ can be an unsubstituted $C_{1-4}$ alkyl (such as those described herein). In some embodiments, one of $R^{4A}$ and $R^{4B}$ can be halogen and the other of $R^{4A}$ and $R^{4B}$ can be an unsubstituted $C_{1-4}$ alkyl (such as those described herein).

In some embodiments, $R^2$ can be

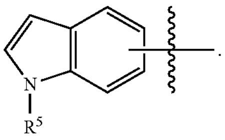

For example, $R^2$ can be

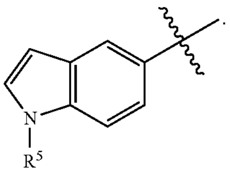

When $R^2$ is

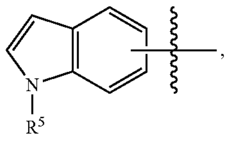

in some embodiments, $R^5$ can be a substituted 5-7 membered monocyclic heterocyclyl. In other embodiments, $R^5$ can be an unsubstituted 5-7 membered monocyclic heterocyclyl. Examples of $R^5$ groups include a substituted or unsubstituted piperidinyl, a substituted or unsubstituted pyrrolidinyl and a substituted or unsubstituted azepanyl. When substituted the $R^5$ group, possible substituents include an unsubstituted $C_{1-4}$ alkyl, halogen, hydroxy and unsubstituted $C_{1-4}$ haloalkyl.

In some embodiments, Ring C can be selected from a substituted or unsubstituted $C_6$-$C_{10}$ aryl, a substituted or unsubstituted monocyclic 5-10 membered heteroaryl, a substituted or unsubstituted monocyclic 5-7 membered carbocyclyl, a substituted or unsubstituted 5-7 membered monocyclic heterocyclyl and a substituted or unsubstituted 7-10 membered bicyclic heterocyclyl.

In some embodiments, Ring C can be a substituted $C_6$-$C_{10}$ aryl. In some embodiments, Ring C can be an unsubstituted $C_6$-$C_{10}$ aryl. In some embodiments, Ring C can be a substituted $C_6$ aryl. In some embodiments, Ring C can be an unsubstituted $C_6$ aryl.

In some embodiments, Ring C can be a substituted 5-10 membered heteroaryl. In some embodiments, Ring C can be an unsubstituted 5-10 membered heteroaryl. In some embodiments, Ring C can be a substituted 5-6 membered heteroaryl. In some embodiments, Ring C can be an unsubstituted 5-6 membered heteroaryl. In some embodiments, Ring C can be selected from furan, thiophene, pyrrole, oxazole, thiazole, imidazole, benzimidazole, indole, pyrazole, isoxazole, pyridine, pyridazine, pyrimidine, pyrazine, purine, quinoline, isoquinoline, quinazoline and quinoxaline; wherein each of the aforementioned groups are substituted or unsubstituted, including any —NH group.

In some embodiments, Ring C can be a substituted or unsubstituted monocyclic 5 membered carbocyclyl. In some embodiments, Ring C can be a substituted or unsubstituted monocyclic 6 membered carbocyclyl. In some embodiments, Ring C can be a substituted or unsubstituted monocyclic 7 membered carbocyclyl.

In some embodiments, Ring C can be a Ring C can be a substituted or unsubstituted 5 membered monocyclic heterocyclyl. In some embodiments, Ring C can be a substituted or unsubstituted 6 membered monocyclic heterocyclyl. In some embodiments, Ring C can be a substituted or unsubstituted 7 membered monocyclic heterocyclyl. In some embodiments, Ring C can be selected from imidazoline, imidazolidine, isoxazoline, isoxazolidine, oxazoline, oxazolidine, oxazolidinone, thiazoline, thiazolidine, morpholine, piperidine, piperazine, pyrrolidine, pyrrolidone, 4-piperidone, pyrazoline, pyrazolidine, tetrahydropyran, azepine, oxepine and diazepine; wherein each of the aforementioned groups are substituted or unsubstituted, including any —NH group.

In some embodiments, Ring C can be a substituted or unsubstituted 7 membered bicyclic heterocyclyl (for example, a fused, a bridged or a spiro heterocyclyl). In some embodiments, Ring C can be a substituted or unsubstituted 8 membered bicyclic heterocyclyl, such as, a fused, a bridged or a spiro heterocyclyl. In some embodiments, Ring C can be a substituted or unsubstituted 9 membered bicyclic heterocyclyl (for example, a fused, a bridged or a spiro heterocyclyl). In some embodiments, Ring C can be a substituted or unsubstituted 10 membered bicyclic heterocyclyl, such as, a fused, a bridged or a spiro heterocyclyl. In some embodiments, Ring C can be selected from pyrrolizidine, indoline, 1,2,3,4 tetrahydroquinoline, 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane; wherein each of the aforementioned groups are substituted or unsubstituted, including any —NH group.

In some embodiments, Ring C can be substituted with one or more substituents independently selected from an unsubstituted $C_1$-$C_6$ alkyl (as described herein) and an unsubstituted ($C_1$-$C_6$ alkyl)acyl. In some embodiments, Ring C can be substituted with one substituent selected from an unsubstituted $C_1$-$C_6$ alkyl (as described herein) and an unsubstituted ($C_1$-$C_6$ alkyl)acyl.

In some embodiments, $R^2$ can be selected from:

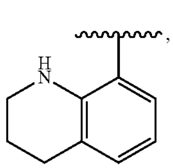
,
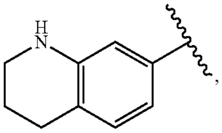
,
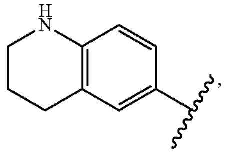
,
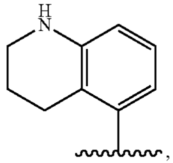
,
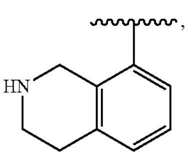
,
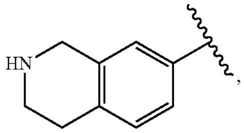
,
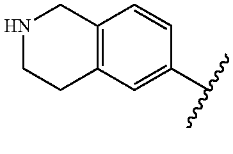
and
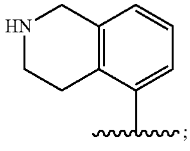
;

wherein each of the aforementioned groups can be substituted or unsubstituted.

A non-limiting list of Bcl-2 inhibitors are described herein, and include those provided in FIG. 1. Further information regarding Bcl-2 inhibitors shown in FIG. 1 are provided in the following publications: WO 2020/089286, WO 2015/011400, U.S. 2014/0199234, WO 2018/027097, WO 2019/210828, WO 2018/192462, WO 2018/127130 and WO 2018/154004, each of which is hereby incorporated by reference for the limited purpose of describing each of the compounds shown in FIG. 1.

Examples of Compound (A) include the following:

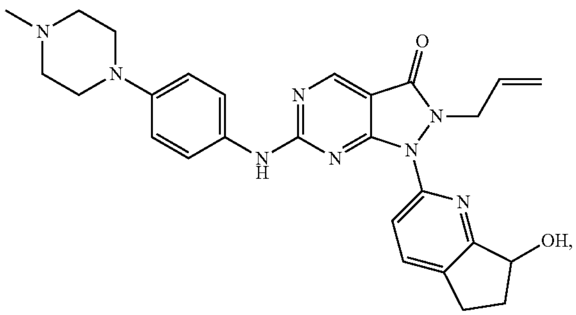
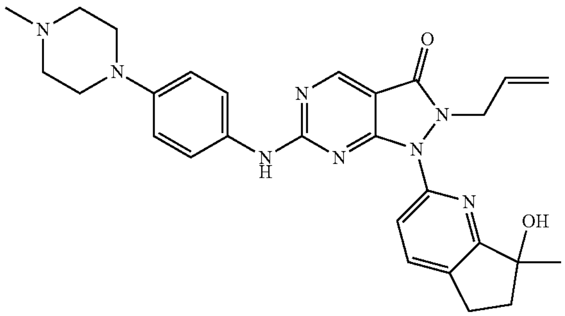
,
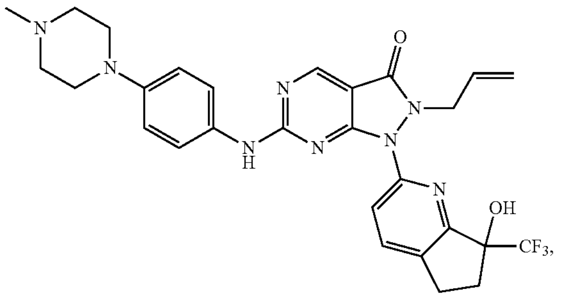
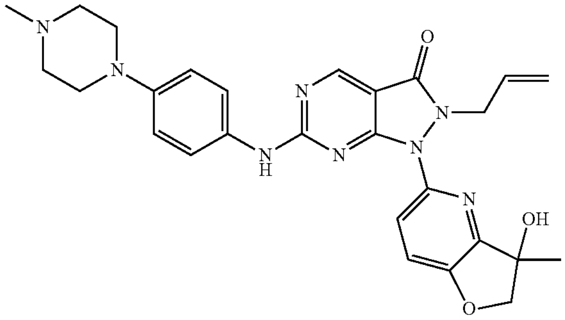
,

-continued
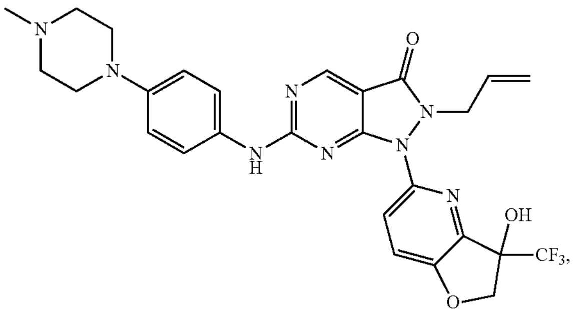
,
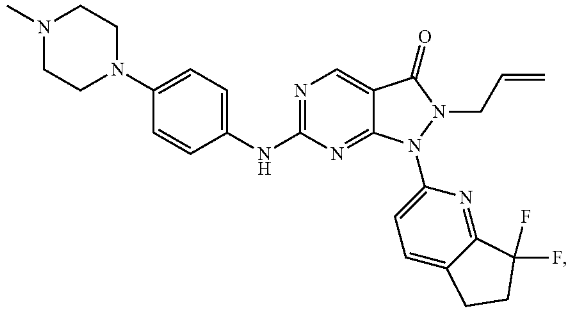
,
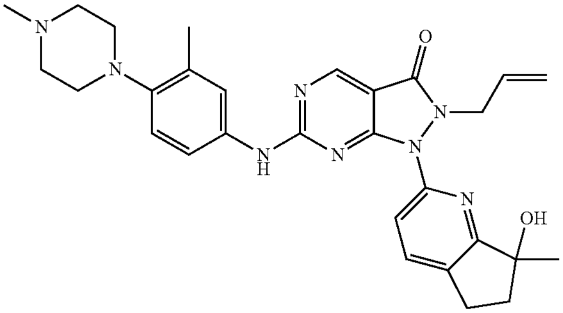
,
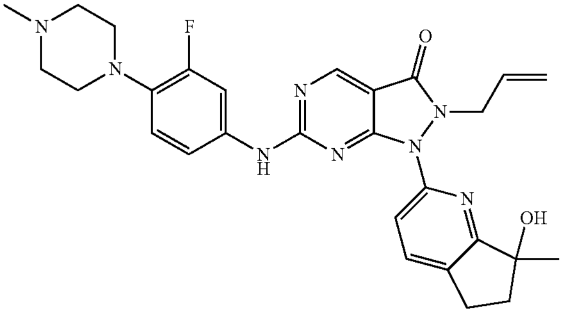
,
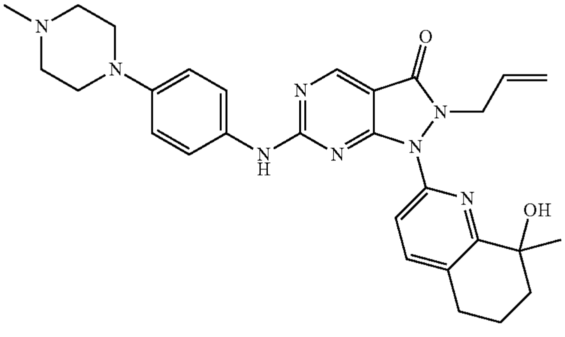
,
-continued
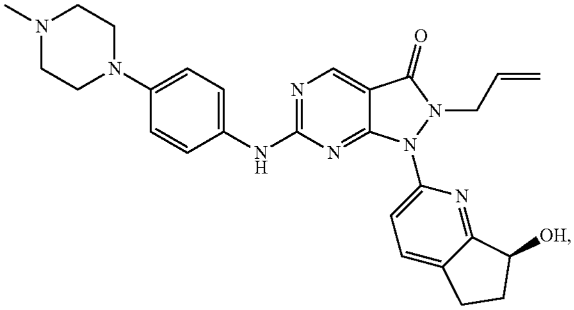
,
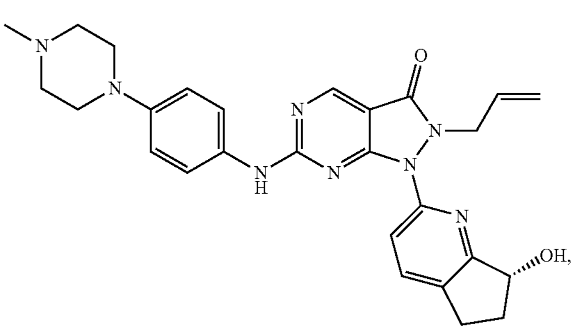
,
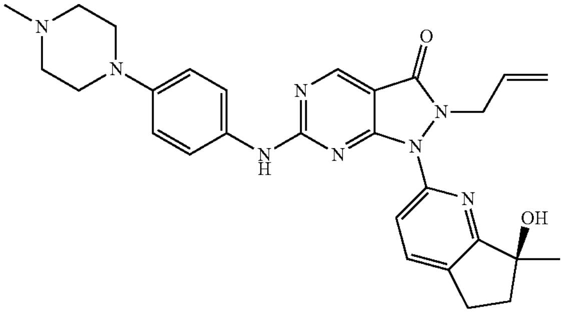
,
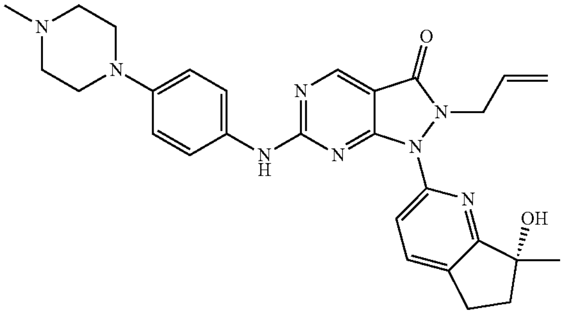
,
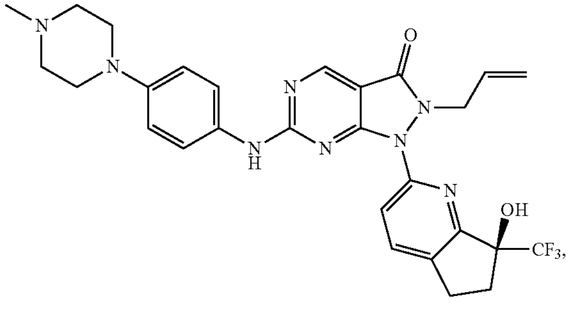
, -continued
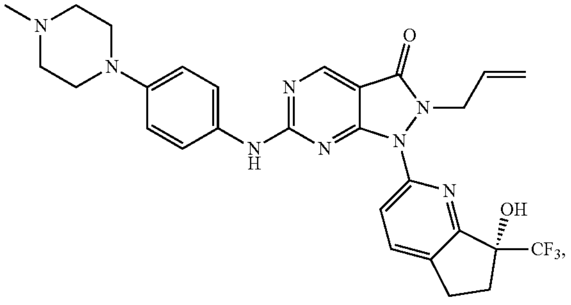
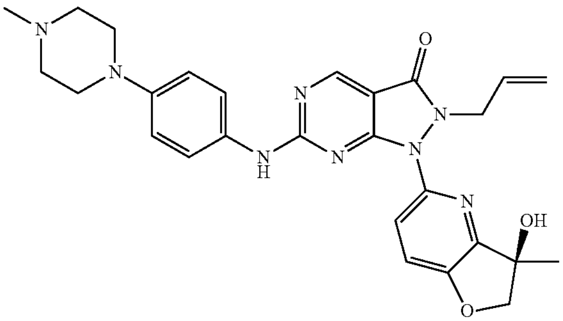
,
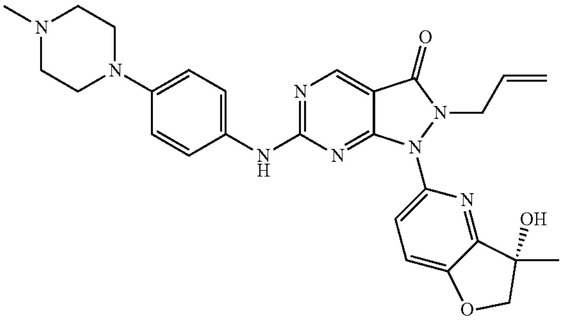
,
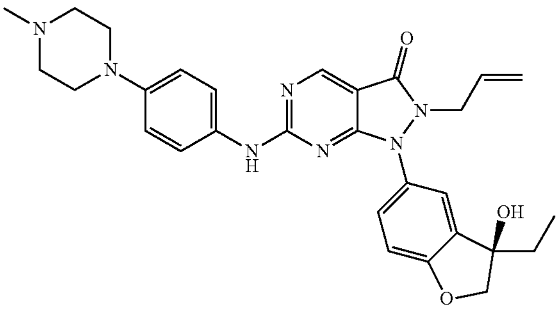
,
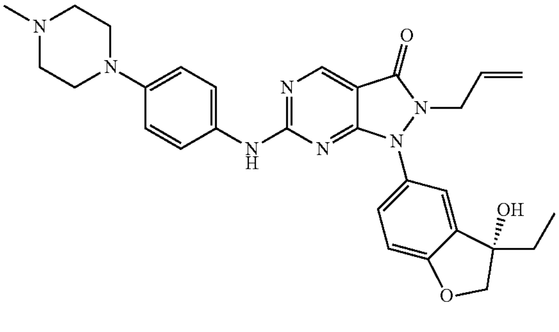
,
-continued
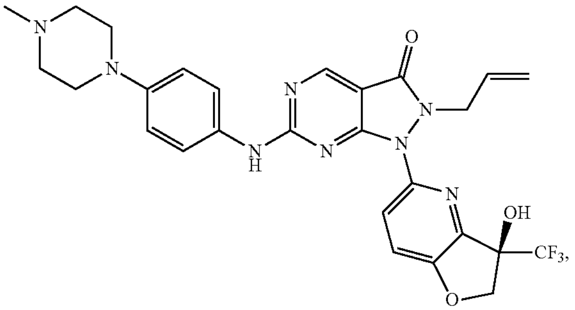
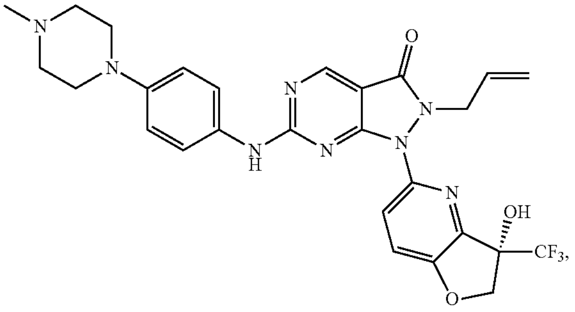
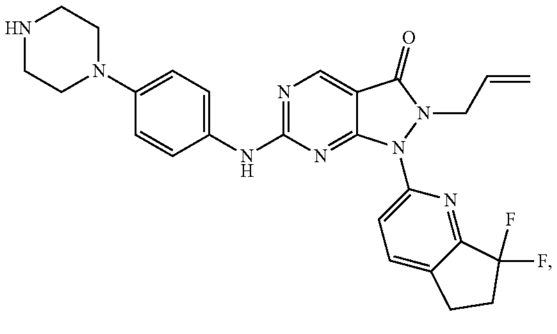
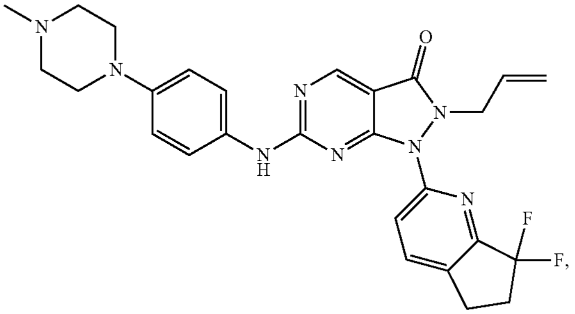
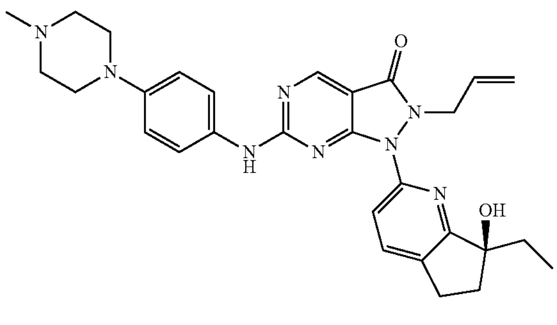
, -continued
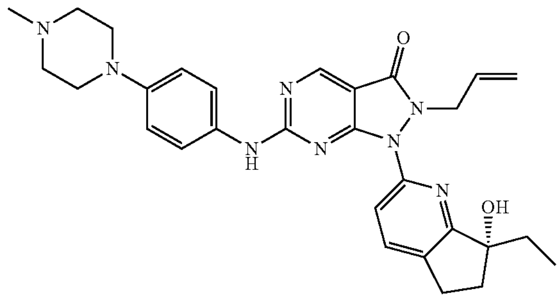
,
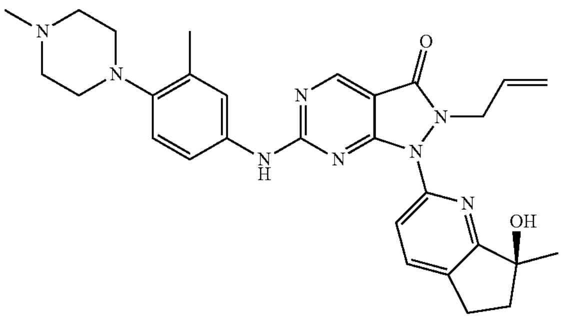
,
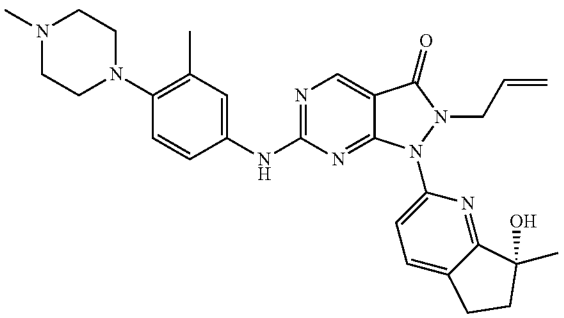
,
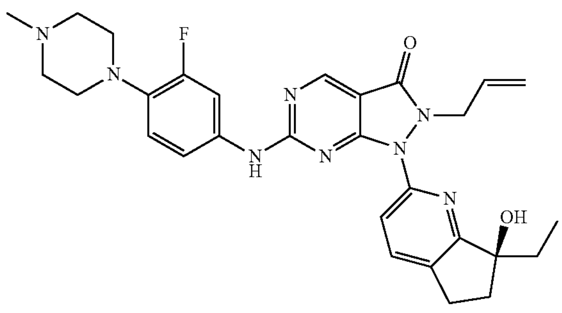
,
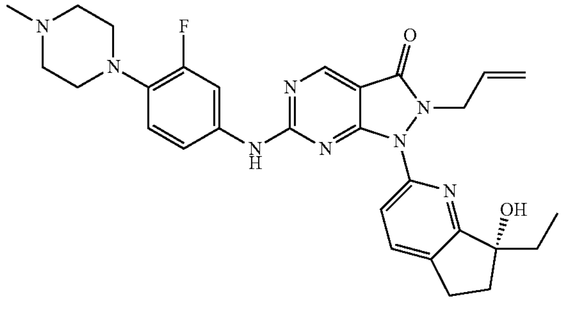
,
-continued
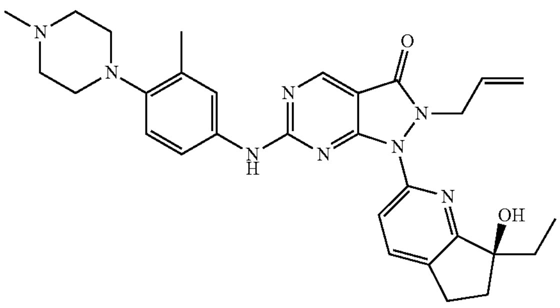
,
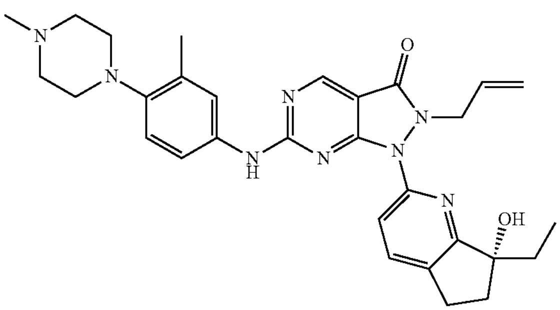
,
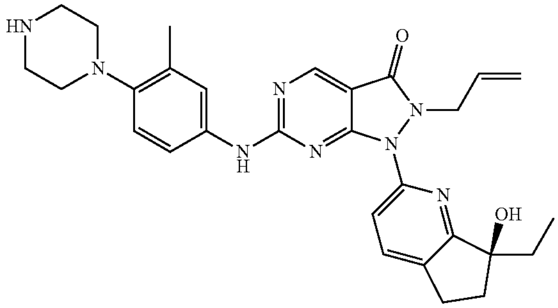
,
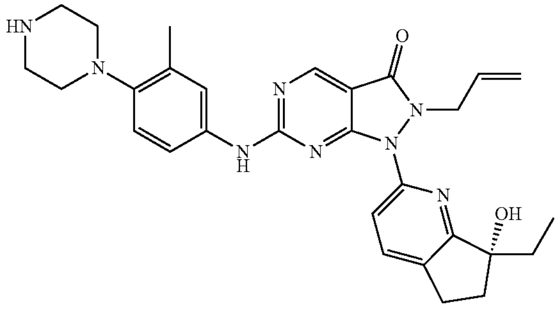
,
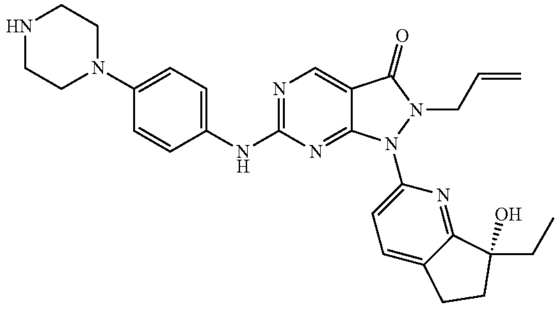
, -continued
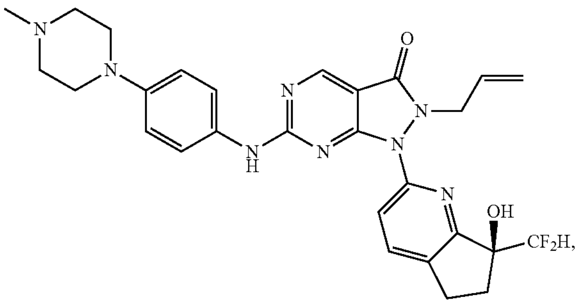
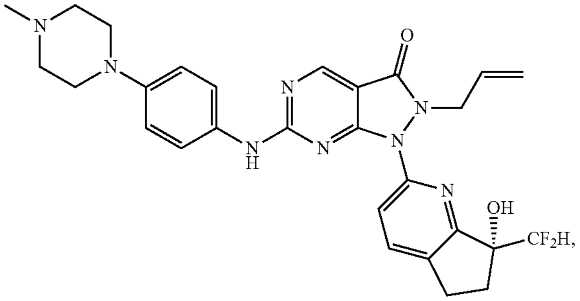
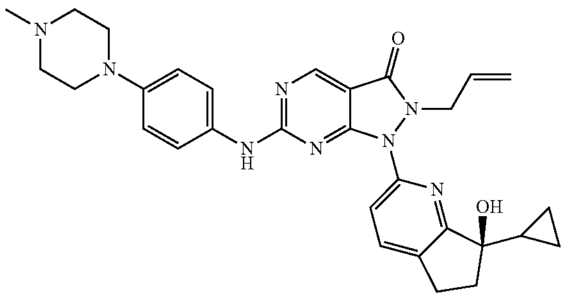
,
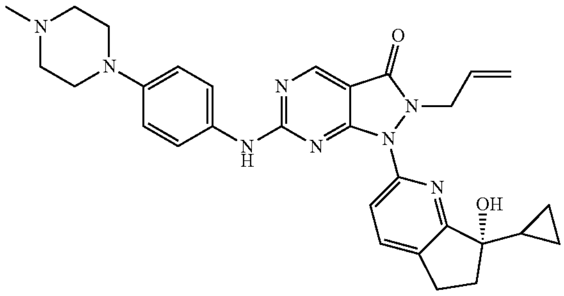
,
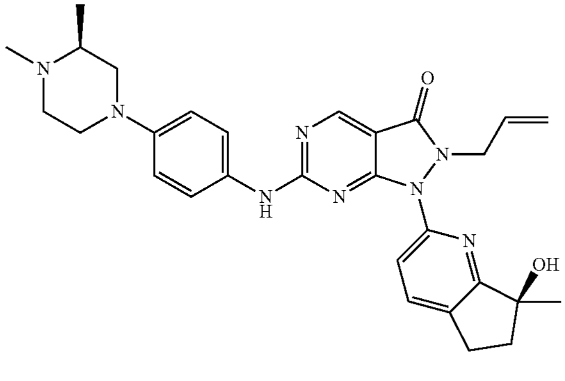
,
-continued
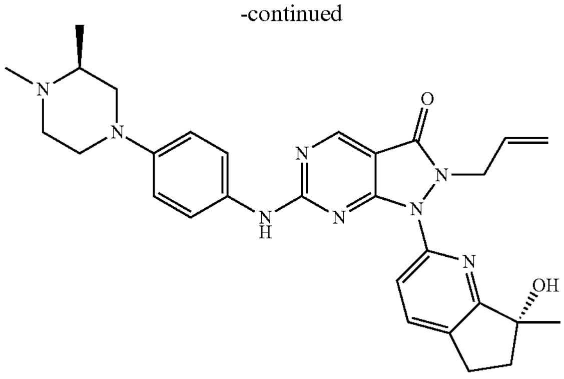
,
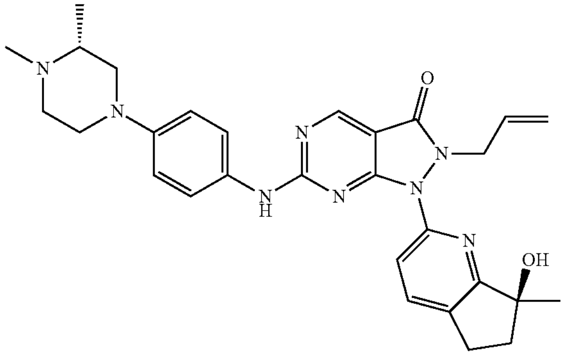
,
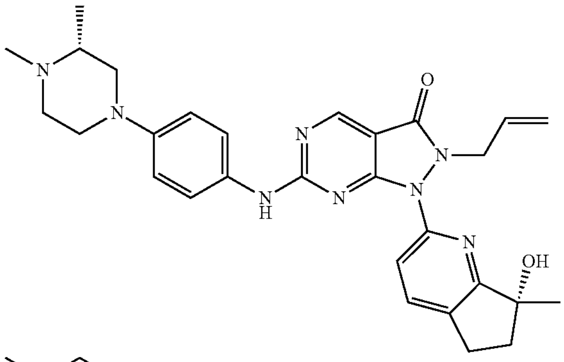
,
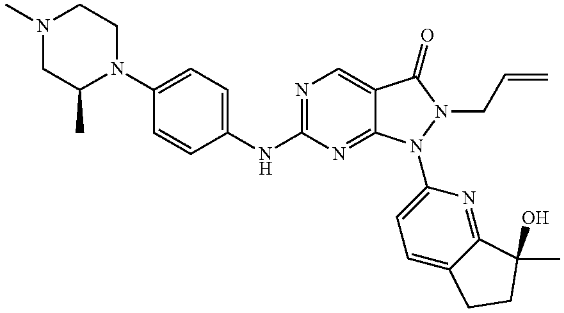
,
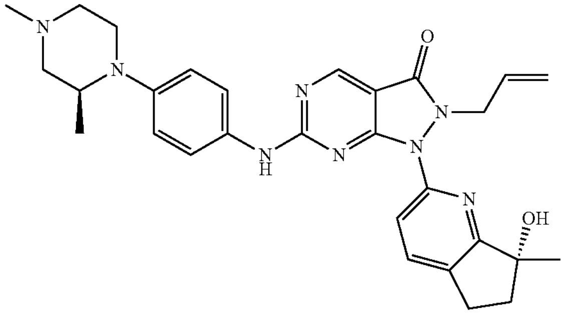
, -continued
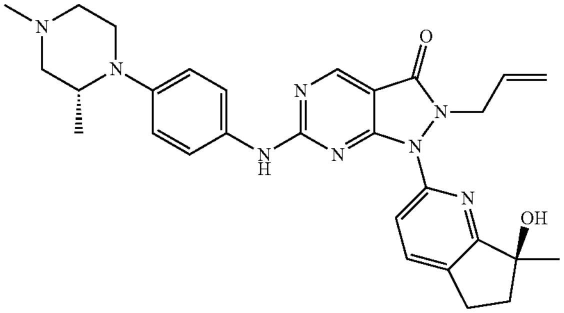
,
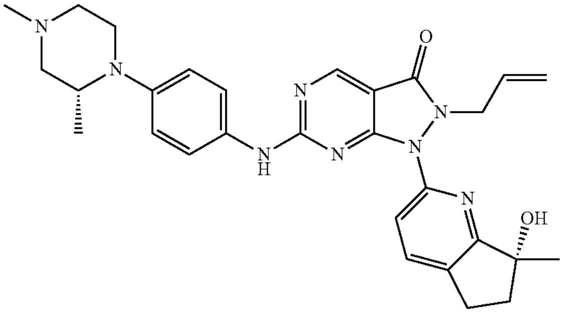
,
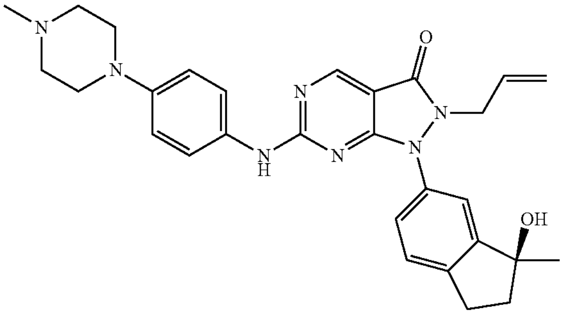
,
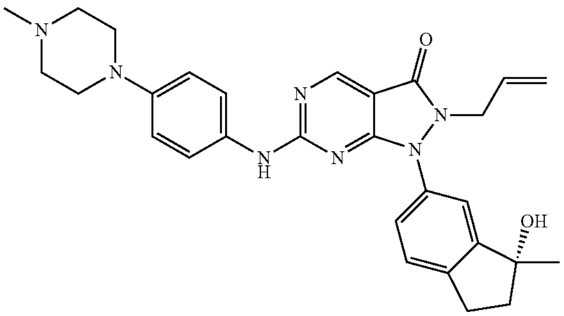
,
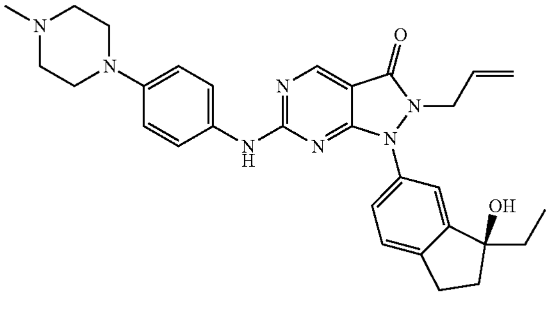
,
-continued
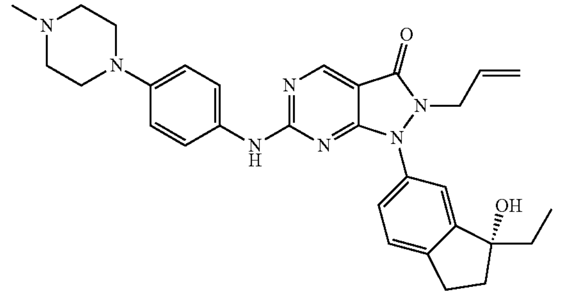
,
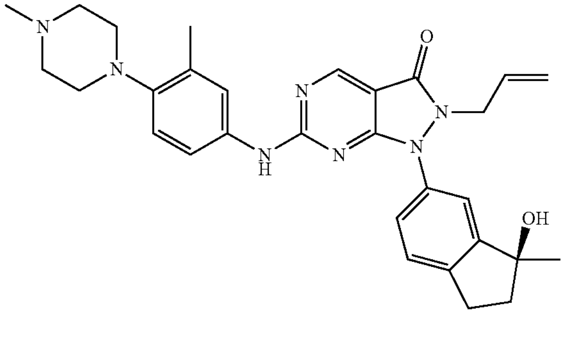
,
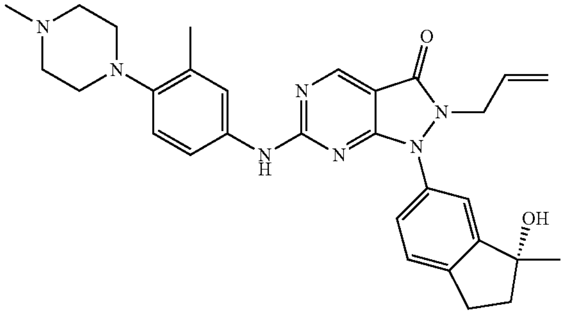
,
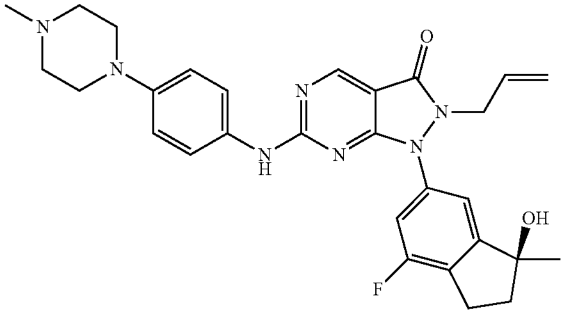
,
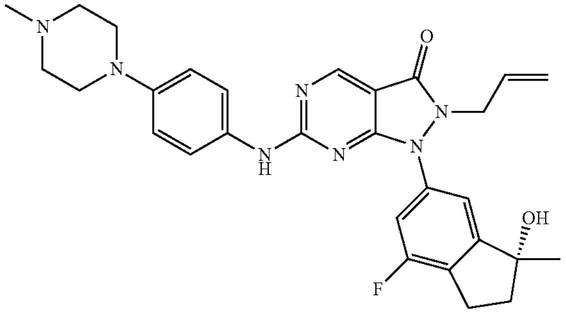
, -continued
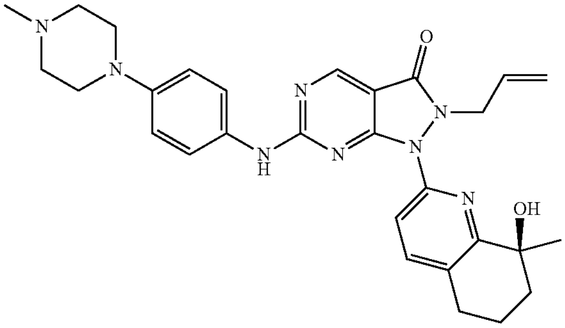
,
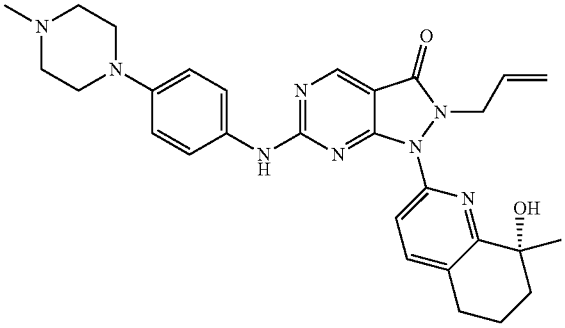
,
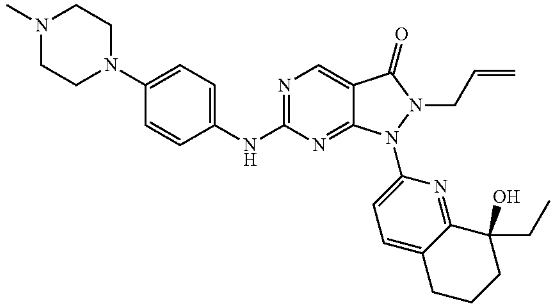
,
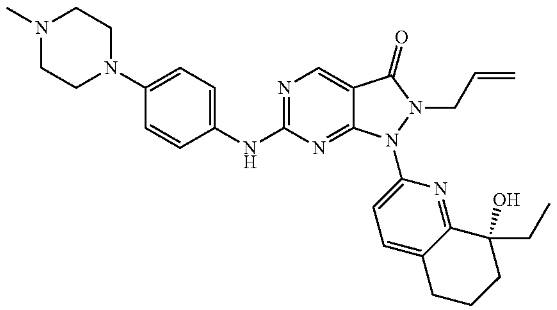
,
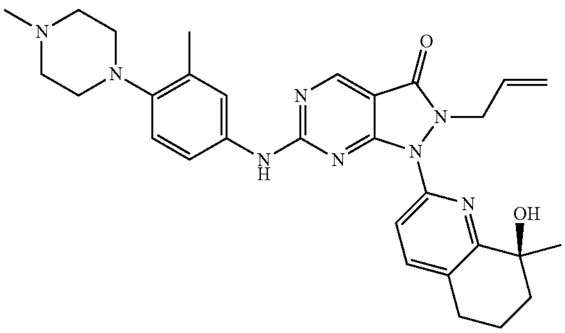
,
-continued
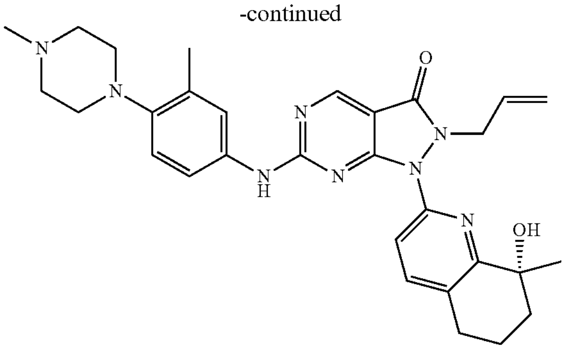
,
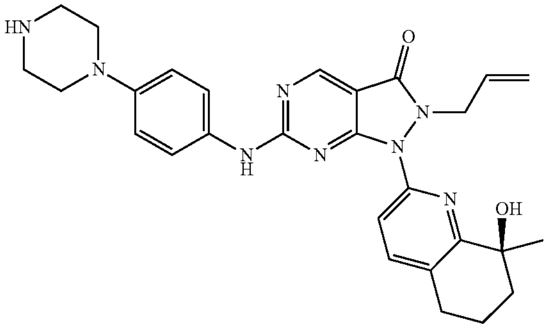
,
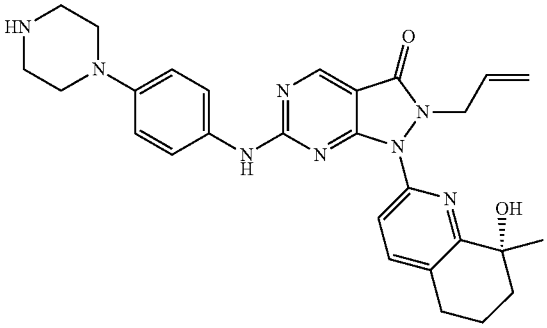
,
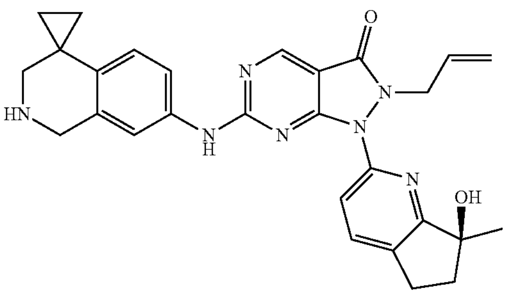
,
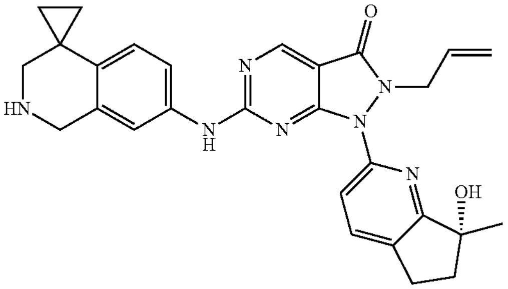
, -continued
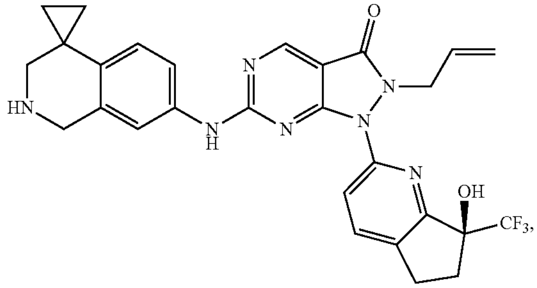
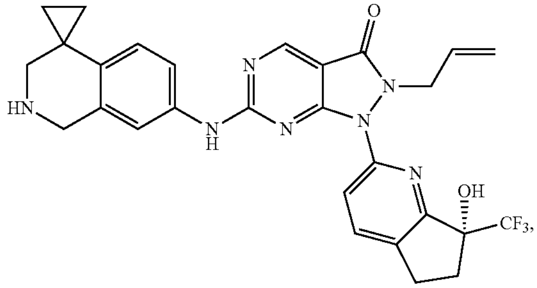
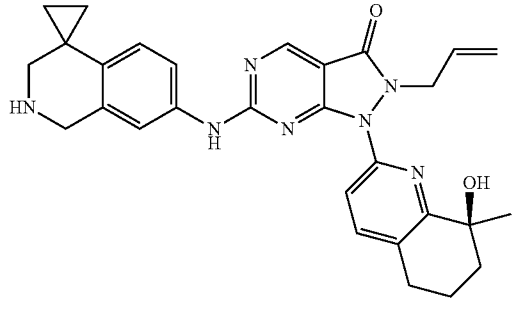
,
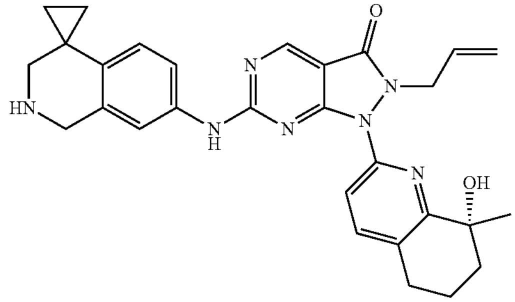
,
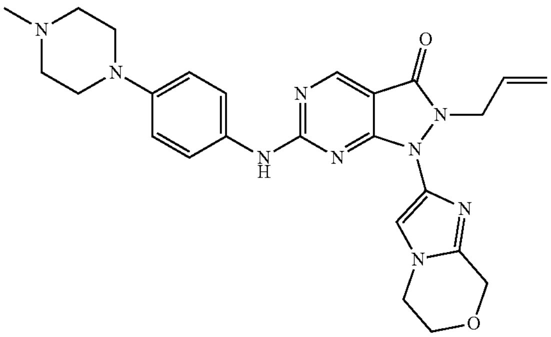
,
-continued
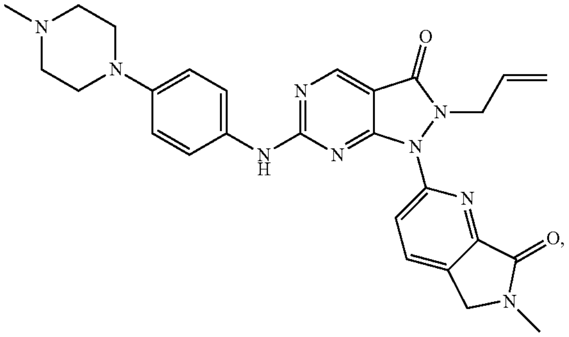
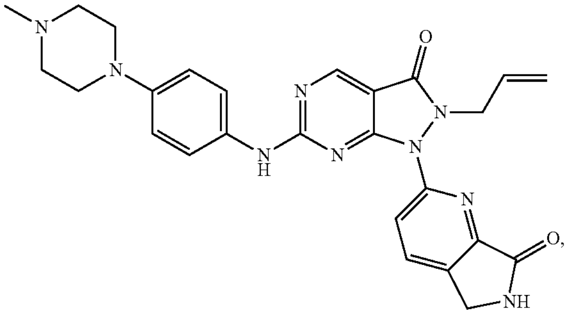
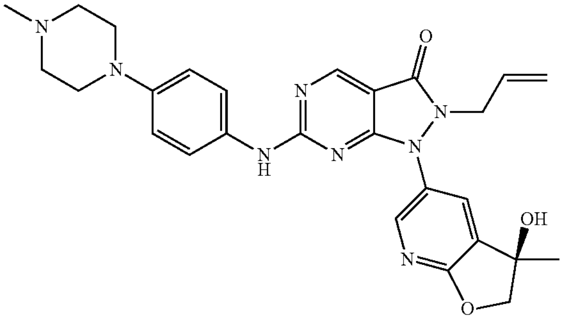
,
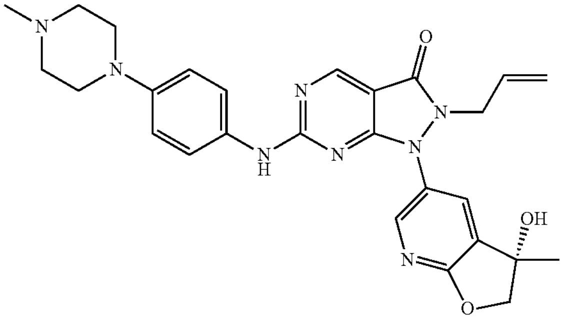
,
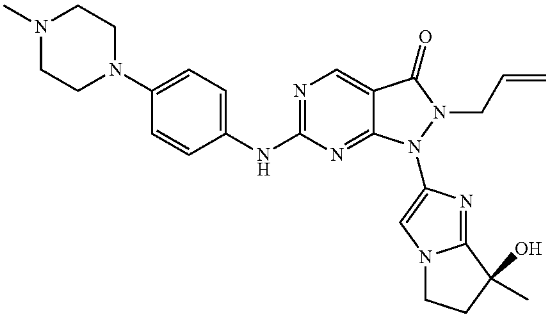
, -continued
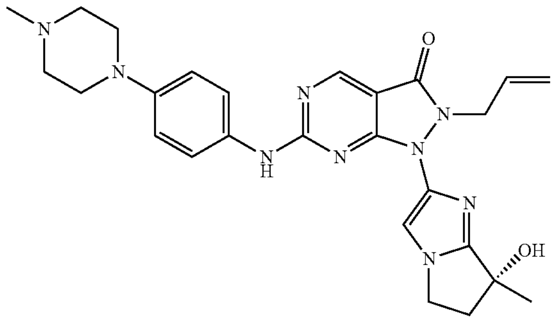
,
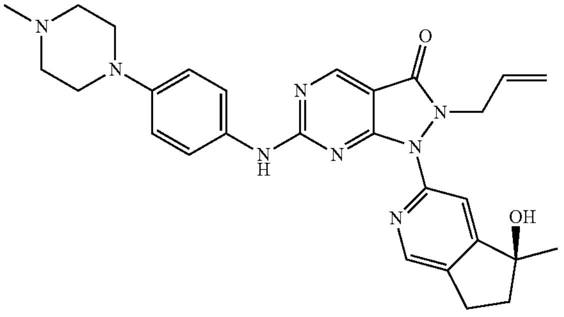
,
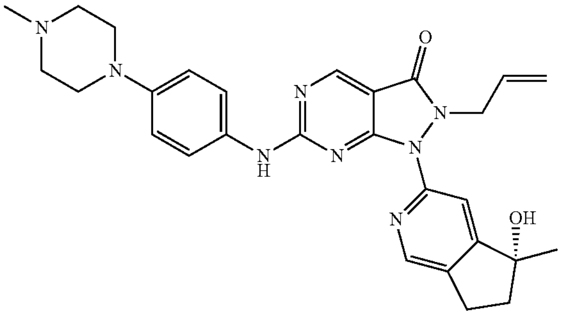
,
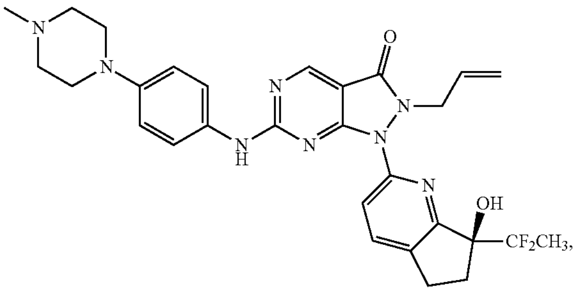
,
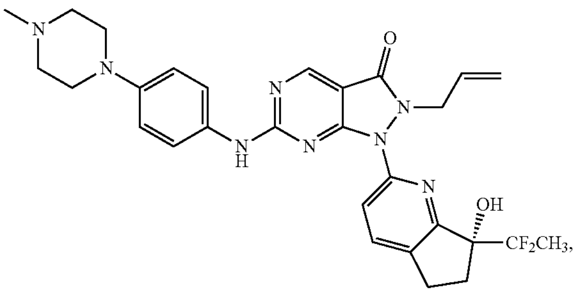
,
-continued
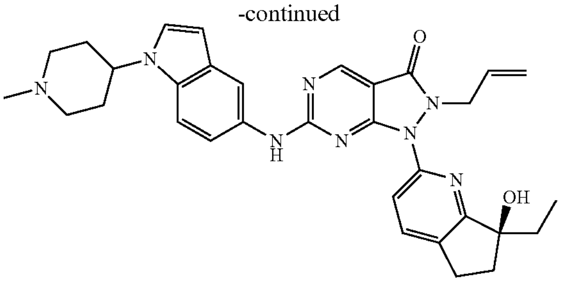
,
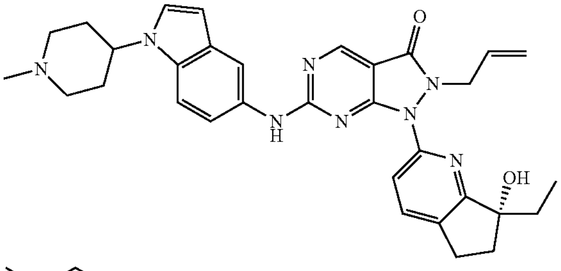
,
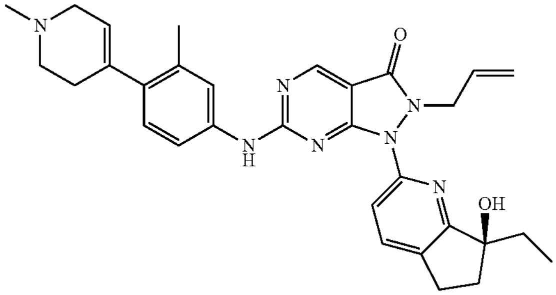
,
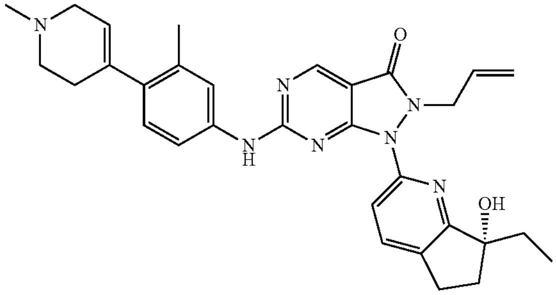
,
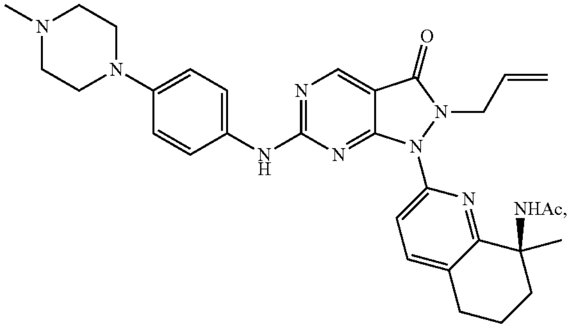
,
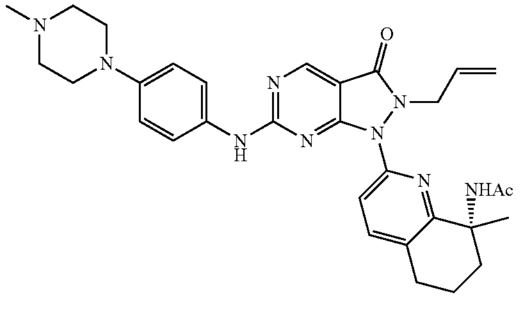
and -continued

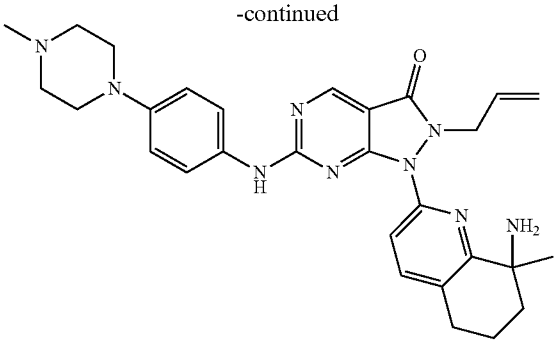

, or a pharmaceutically acceptable salt of any of any of the foregoing.

Compound (A), along with pharmaceutically acceptable salts thereof, can be prepared as described herein and in WO 2019/173082, which is hereby incorporated by reference in its entirety. As described in WO 2019/173082, Compound (A) is a WEE1 inhibitor.

Figure 2:
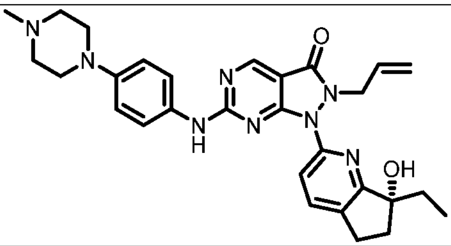
Figure 2:
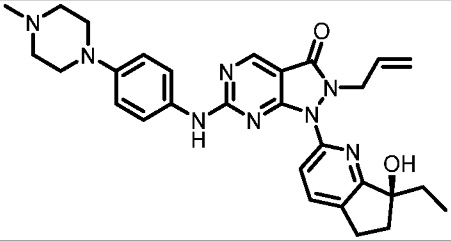
Figure 2:
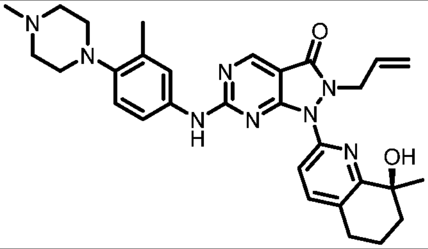
Figure 2:
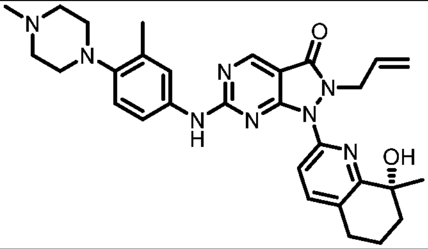
Figure 2:
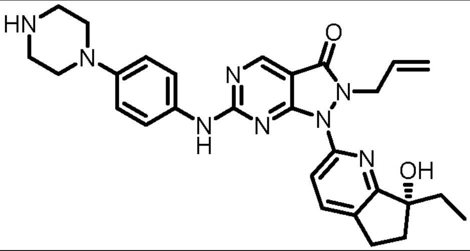
Figure 2:
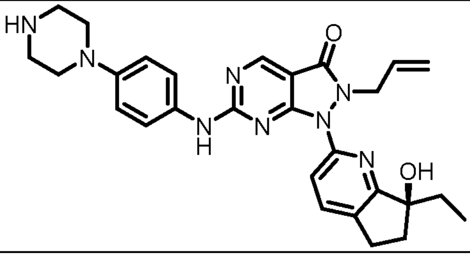
Figure 2:
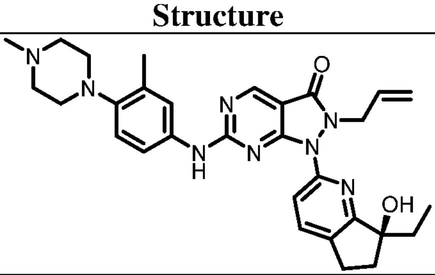
Figure 2:
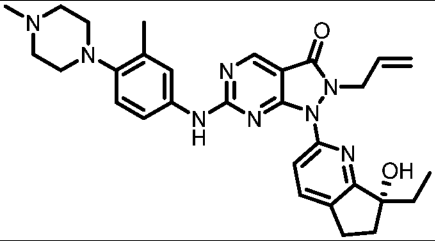
Figure 2:
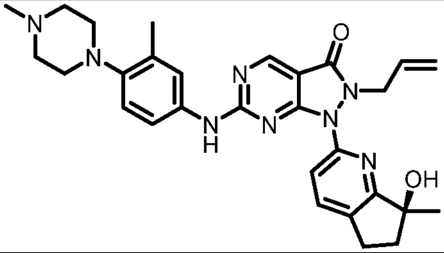
Figure 2:
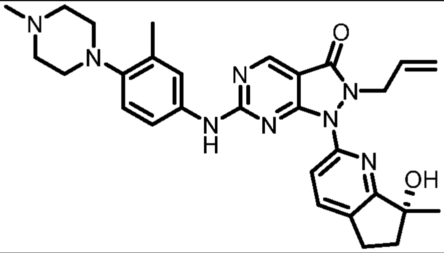
Figure 2:
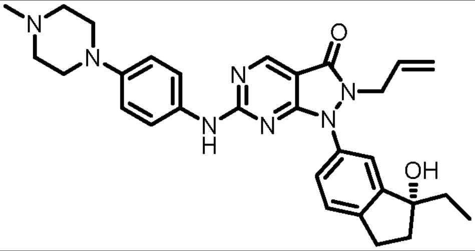
Figure 2:
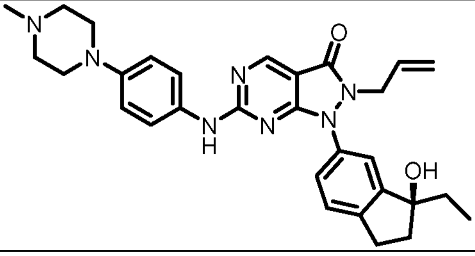

Embodiments of combinations of Compound (A) and Compound (B), including pharmaceutically acceptable salts of any of the foregoing, are provided in Table 1. The numbers in Table 1 represent a compound as provided in FIGS. 1 and 2. For example, in Table 1, a combination represented by 3:5A corresponds to a combination of

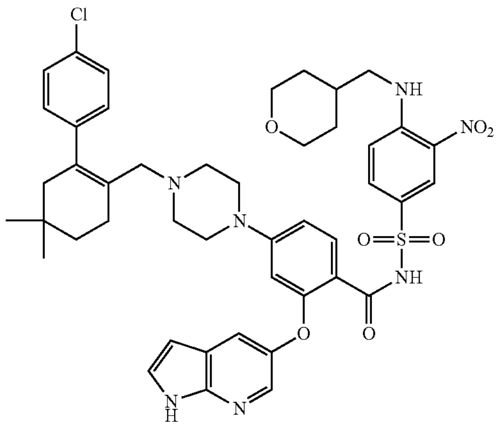

and

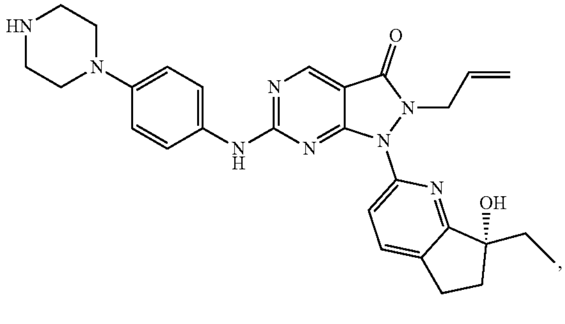

, including pharmaceutically acceptable salts of any of the foregoing.

TABLE 1

| Cmpd:Cmpd | Cmpd:Cmpd | Cmpd:Cmpd | Cmpd:Cmpd |
|---|---|---|---|
| 1:1A | 1:4A | 1:7A | 1:10A |
| 2:1A | 2:4A | 2:7A | 2:10A |
| 3:1A | 3:4A | 3:7A | 3:10A |
| 4:1A | 4:4A | 4:7A | 4:10A |
| 5:1A | 5:4A | 5:7A | 5:10A |
| 6:1A | 6:4A | 6:7A | 6:10A |
| 7:1A | 7:4A | 7:7A | 7:10A |
| 8:1A | 8:4A | 8:7A | 8:10A |
| 9:1A | 9:4A | 9:7A | 9:10A |
| 1:2A | 1:5A | 1:8A | 1:11A |
| 2:2A | 2:5A | 2:8A | 2:11A |
| 3:2A | 3:5A | 3:8A | 3:11A |
| 4:2A | 4:5A | 4:8A | 4:11A |
| 5:2A | 5:5A | 5:8A | 5:11A |
| 6:2A | 6:5A | 6:8A | 6:11A |
| 7:2A | 7:5A | 7:8A | 7:11A |
| 8:2A | 8:5A | 8:8A | 8:11A |
| 9:2A | 9:5A | 9:8A | 9:11A |
| 1:3A | 1:6A | 1:9A | 1:12A |
| 2:3A | 2:6A | 2:9A | 2:12A |
| 3:3A | 3:6A | 3:9A | 3:12A |
| 4:3A | 4:6A | 4:9A | 4:12A |
| 5:3A | 5:6A | 5:9A | 5:12A |
| 6:3A | 6:6A | 6:9A | 6:12A |
| 7:3A | 7:6A | 7:9A | 7:12A |
| 8:3A | 8:6A | 8:9A | 8:12A |
| 9:3A | 9:6A | 9:9A | 9:12A |

The order of administration of compounds in a combination described herein can vary. In some embodiments, Compound (A), including pharmaceutically acceptable salts thereof, can be administered prior to all of Compound (B), or a pharmaceutically acceptable salt thereof. In other embodiments, Compound (A), including pharmaceutically acceptable salts thereof, can be administered prior to at least one Compound (B), or a pharmaceutically acceptable salt thereof. In still other embodiments, Compound (A), including pharmaceutically acceptable salts thereof, can be administered concomitantly with Compound (B), or a pharmaceutically acceptable salt thereof. In yet still other embodiments, Compound (A), including pharmaceutically acceptable salts thereof, can be administered subsequent to the administration of at least one Compound (B), or a pharmaceutically acceptable salt thereof. In some embodiments, Compound (A), including pharmaceutically acceptable salts thereof, can be administered subsequent to the administration of all Compound (B), or a pharmaceutically acceptable salt thereof.

There may be several advantages for using a combination of compounds described herein. For example, combining compounds that attack multiple pathways at the same time, can be more effective in treating a cancer, such as those described herein, compared to when the compounds of combination are used as monotherapy.

In some embodiments, a combination as described herein of Compound (A), including pharmaceutically acceptable salts thereof, and one or more of Compound (B), or pharmaceutically acceptable salts thereof, can decrease the number and/or severity of side effects that can be attributed to a compound described herein, such as Compound (B), or a pharmaceutically acceptable salt thereof.

Using a combination of compounds described herein can results in additive, synergistic or strongly synergistic effect. A combination of compounds described herein can result in an effect that is not antagonistic.

In some embodiments, a combination as described herein of Compound (A), including pharmaceutically acceptable salts thereof, and one or more of Compound (B), or pharmaceutically acceptable salts thereof, can result in an additive effect. In some embodiments, a combination as described herein of Compound (A), including pharmaceutically acceptable salts thereof, and one or more of Compound (B), or pharmaceutically acceptable salts thereof, can result in a synergistic effect. In some embodiments, a combination as described herein of Compound (A), including pharmaceutically acceptable salts thereof, and one or more of Compound (B), or pharmaceutically acceptable salts thereof, can result in a strongly synergistic effect. In some embodiments, a combination as described herein of Compound (A), including pharmaceutically acceptable salts thereof, and one or more of Compound (B), or pharmaceutically acceptable salts thereof, is not antagonistic.

As used herein, the term "antagonistic" means that the activity of the combination of compounds is less compared to the sum of the activities of the compounds in combination when the activity of each compound is determined individually (i.e., as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compounds in the combination when the activity of each compound is determined individually.

A potential advantage of utilizing a combination as described herein may be a reduction in the required amount(s) of the compound(s) that is effective in treating a disease condition disclosed herein compared to when each compound is administered as a monotherapy. For example, the amount of Compound (B), or a pharmaceutically acceptable salt thereof, used in a combination described herein can be less compared to the amount of Compound (B), or a pharmaceutically acceptable salt thereof, needed to achieve the same reduction in a disease marker (for example, tumor size) when administered as a monotherapy. Another potential advantage of utilizing a combination as described herein is that the use of two or more compounds having different mechanisms of action can create a higher barrier to the development of resistance compared to when a compound is administered as monotherapy. Additional advantages of utilizing a combination as described herein may include little to no cross resistance between the compounds of a combination described herein; different routes for elimination of the compounds of a combination described herein; and/or little to no overlapping toxicities between the compounds of a combination described herein.

Pharmaceutical Compositions

Compound (A), including pharmaceutically acceptable salts thereof, can be provided in a pharmaceutical composition. Likewise, Compound (B), including pharmaceutically acceptable salts thereof, can be provided in a pharmaceutical composition.

The term "pharmaceutical composition" refers to a mixture of one or more compounds and/or salts disclosed herein with other chemical components, such as diluents, carriers and/or excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as antioxidants and metal-chelating agents are excipients. In an embodiment, the pharmaceutical composition comprises an anti-oxidant and/or a metal-chelating agent. A "diluent" is a type of excipient.

In some embodiments, Compounds (B), along with pharmaceutically acceptable salts thereof, can be provided in a pharmaceutical composition that includes Compound (A), including pharmaceutically acceptable salts thereof. In other embodiments, Compound (B), along with pharmaceutically acceptable salts thereof, can be administered in a pharmaceutical composition that is separate from a pharmaceutical composition that includes Compound (A), including pharmaceutically acceptable salts thereof.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, Compound (A), including pharmaceutically acceptable salts thereof, can be administered orally. In some embodiments, Compound (A), including pharmaceutically acceptable salts thereof, can be provided to a subject by the same route of administration as Compound (B), along with pharmaceutically acceptable salts thereof. In other embodiments, Compound (A), including pharmaceutically acceptable salts thereof, can be provided to a subject by a different route of administration as Compound (B), along with pharmaceutically acceptable salts thereof.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

Uses and Methods of Treatment

As provided herein, in some embodiments, a combination of compounds that includes an effective amount of Compound (A), including pharmaceutically acceptable salts thereof, and an effective amount of one or more of Compound (B), or a pharmaceutically acceptable salt thereof, can be used to treat a disease or condition.

Examples of diseases or conditions that can be treated by a combination of compounds, along with pharmaceutically acceptable salts, include malignancies, cancers and syndromes such as those described herein. In some embodiments, the disease or condition can be a hematological malignancy. Exemplary hematological malignancies include is a leukemia, a lymphoma, or a myeloma. In some embodiments, the hematological malignancy can be refractory. In some embodiments, the disease or condition can be a leukemia including, but not limited to: acute myeloid leukemia (AML) (including its subtypes, such as, subtypes TP53 wildtype AML, TP53 mutant AML, refractory AML, acute promyelocytic leukemia, acute basophilic leukemia, and therapy-related AML), chronic lymphocytic leukemia (CLL) (including, but not limited to hairy cell leukemia and small lymphocytic lymphoma), acute lymphoblastic leukemia (ALL) (including, but not limited to specification for B-cell, T-cell, and ETP) and chronic myeloid leukemia (CML) (chronic myelogenous leukemia).

In some embodiments, the disease or condition can be a Myelodysplastic syndrome. In some embodiments, the disease or condition can be a myeloproliferative neoplasm (MPN), such as polycythemia vera (PV), myelofibrosis (MF) and essential thrombocythemia (ET).

As described herein, a combination of compounds described herein can be used to treat and/or ameliorate a lymphoma. Exemplary lymphomas include, but are not limited to, a non-Hodgkin's lymphoma (NHL) (including, but not limited to mantle cell lymphoma (MCL), diffuse large B-cell lymphoma (DLBCL), follicular lymphoma (FL), marginal zone lymphoma (MZL), peripheral T-cell lymphoma, cutaneous T-cell lymphoma, NK lymphoma, Burkitt lymphoma and Waldenstrom's macroglobulinemia). A combination of compounds, including pharmaceutically acceptable salts thereof, can also be used to treat a myeloma. Examples of myelomas that can be treated include, but are not limited to, multiple myeloma (MM) (including but not limited to translocation(11;14) and non-translocation(11;14)). As described herein, a combination of compounds described herein can be used to treat and/or ameliorate a systemic mastocytosis, and blastic plasmacytoid dendritic cell neoplasm.

A disease or condition described herein can be in an adult or pediatric subject. In some embodiments, the subject that suffers from the disease or condition, such as those described herein, can be a pediatric subject. In some embodiments, the disease or condition can be a pediatric hematological malignancy, for example, pediatric AML and/or pediatric ALL.

A combination of compounds described herein can be used to treat and/or ameliorate a solid tumor. For example, in some embodiments, the solid tumor can be selected from an Ewing's tumor and a Wilms' cancer. Additional examples of a solid tumor that can be treated by a combination of compounds described herein, including pharmaceutically acceptable salts thereof, are a bladder cancer, a brain cancer, a breast cancer (including but not limited to ER+ breast cancer and triple negative breast cancer), a cervical cancer, a choriocarcinoma, a cervicocerebral cancer, a colon cancer, an endometrial cancer, an esophageal cancer, a gallbladder/bile duct cancer, a head and neck cancer (including oral cancer), a hepatocellular cancer, a lung cancer (including a non-small cell cancer and small-cell lung cancer), a mesothelioma, an ovarian cancer, an osteosarcoma, a pancreatic cancer, a penis cancer, an anal cancer, a prostate cancer, a small cell cancer, a stomach cancer, a rectal cancer, a renal pelvis/ureter cancer, a skin cancer, a soft tissue sarcoma, a stomach cancer, a testicular cancer, a thyroid cancer, an uterus body cancer, and an uterocervical cancer. In some embodiments, the disease or condition can be a cancer that expresses BCL-2 protein.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The term "effective amount" is used to indicate an amount of an active compound, or pharmaceutical agent, that elicits the biological or medicinal response indicated. For example, an effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor.

The amount of compound, salt and/or composition required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of compounds (A) and/or (B), or pharmaceutically acceptable salts of any of the foregoing, can be determined by comparing their in vitro activity, and in vivo activity in animal models. Such comparison can be done by comparison against an established drug, such as cisplatin and/or gemcitabine)

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

CTG Assay

Cell proliferation was measured using the CellTiter-Glo® Luminescent Cell Viability Assay. The assay involved the addition of a single reagent (CellTiter-Glo® Reagent) directly to cells cultured in serum-supplemented medium. DMS-53 (ATCC, CRL-2062) cells were cultured according to ATCC recommendations and were seeded at 20,000 cells per well.

Figure 3:
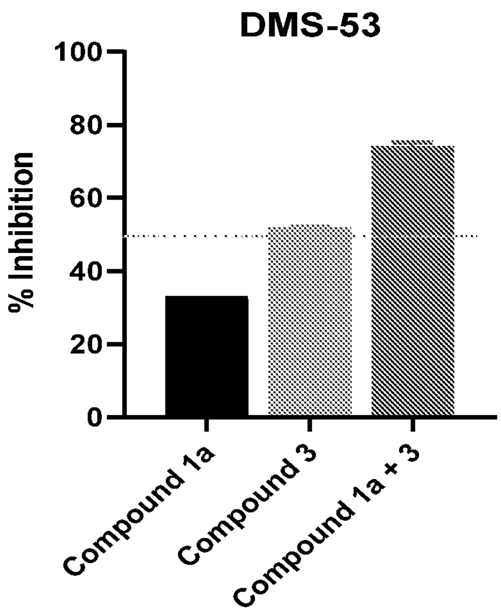
FIG. 3 shows the percent inhibition of Compound 1a and Compound 3 as single agents and in combination against DMS-53 (lung cancer cell line).

Each compound evaluated was prepared as a DMSO stock solution (10 mM). Compounds were tested in duplicate on each plate, using the concentration indicated in Table 2. Compound treatment (10.0 μL) was added to the cells from a 10× stock concentration of each compound. Plates were incubated at 37° C., 5% $CO_2$ for 72 h and then equilibrated at room temperature for approximately 30 min. An equal-volume amount of CellTiter-Glo® Reagent (100 μL) was added to each well. Plates were mixed for 2 mins on an orbital shaker to induce cell lysis and then incubated at room temperature for 10 mins to stabilize the luminescent signal. Luminescence was recorded using a SpectraMAX, M5e plate reader according to CellTiter-Glo protocol. Percent inhibition was calculated using the following formula: % inhibition=(RLU*100/(RLU of the cell background)). FIG. 3 and Table 2 illustrate that the addition of Compound 3 to Compound 1a (alternatively referred to as "Compound 1A" throughout the specification and figures) resulted in combination efficacy.

TABLE 2

| | DMS-53 | |
| --- | --- | --- |
| | Concentration (nM) | Inhibition (%) |
| Compound 3 | 370 | 52 |
| Compound 1A | 650 | 33 |
| Compound 3 + Compound 1A | 370 + 650 | 74 |

Xenograft Tumor Model

Figure 4:
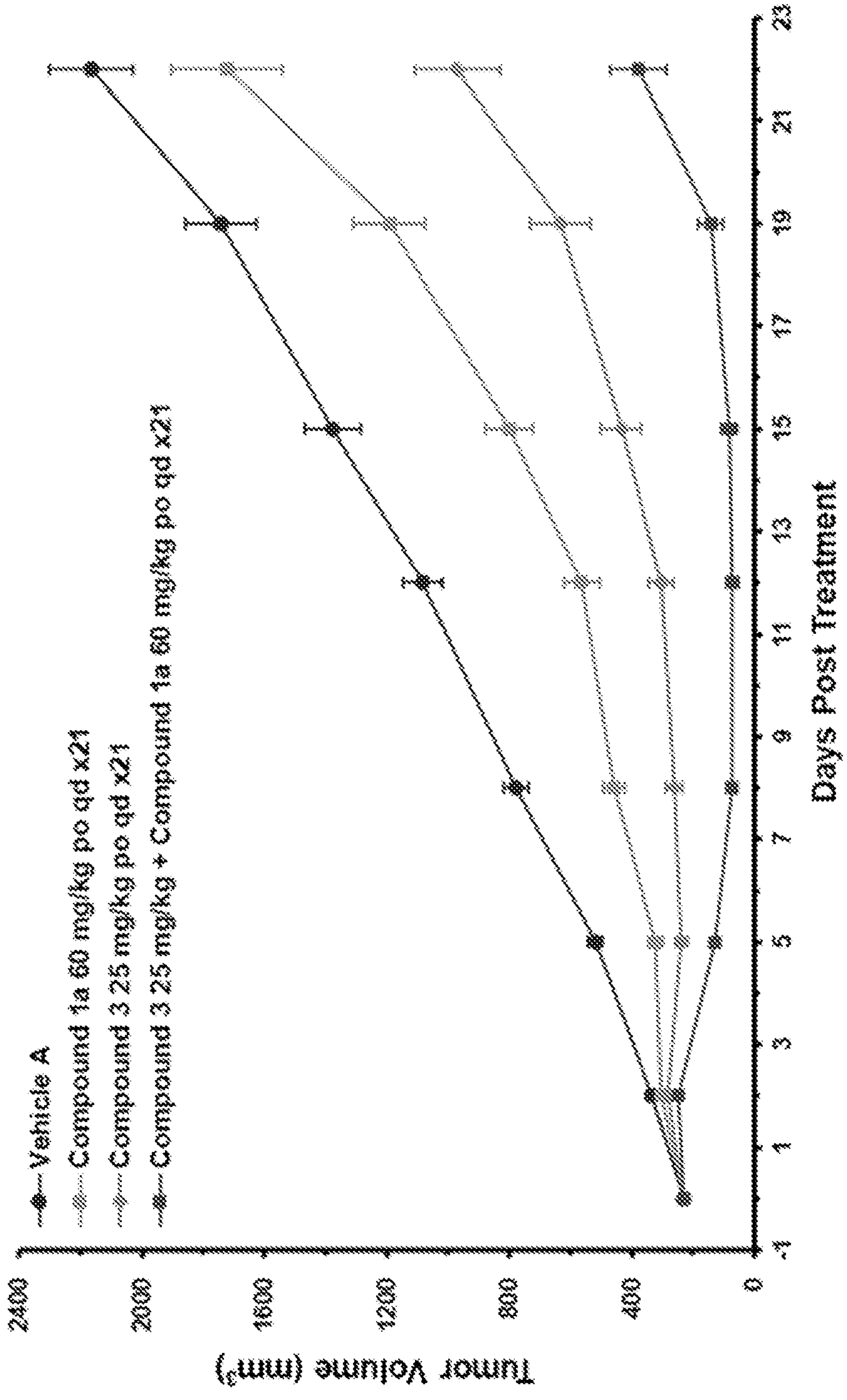
FIG. 4 shows the results of a tumor growth study in response to monotherapy and combination therapy with Compound 1a and Compound 3 in an MV4-11 mouse model.

MV4-11 cells were cultured in vitro in IMDM Medium supplemented with 10% fetal bovine serum at 37° C. in an atmosphere of 5% $CO_2$ in air. The cells growing in an exponential growth phase were harvested and counted for tumor inoculation. Mice were inoculated with MV4-11 cells subcutaneously on the right flank with the single cell suspension of 95% viable tumor cells ($1\times10^7$) in 100 μL IMDM without serum for the tumor development without serum for the tumor development. The treatment was started when the mean tumor size reached approximately 230 $mm^3$, with individual tumor size ranging from 200-260 $mm^3$. Animals were randomly distributed into treatment groups of 10 animals each and dosed orally for 21 days as follows: vehicle at same volume as the single agent treatment; Compound 1a at 60 mg/kg, Compound 3 at 25 mg/kg and the and the combination treatment of Compound 1a (60 mg/kg) and Compound 3 (25 mg/kg). Tumor volumes were evaluated twice per week to calculate tumor volume over time, and mice are weighed twice per week as a surrogate for signs of toxicity. Tumor growth inhibition (TGI) was calculated using the following equation $TGI=(1-(Td-T0)/(Cd-C0))\times100\%$. Td and Cd are the mean tumor volumes of the treated and control animals, and T0 and C0 are the mean tumor volumes of the treated and control animals at the start of the experiment. FIG. 4 illustrates that single agent treatment of Compound 1a at 60 mg/kg resulted in minor tumor growth inhibition (20%) and single agent treatment with Compound 3 resulted in efficacy around (50%). In FIG. 4, the bottom line (squares) represents the data for the combination of Compound 3 (25 mg/kg) and Compound 1a (60 mg/kg) and the third line from the bottom (squares) represents data for Compound 1a (60 mg/kg). The combination of Compound 3 (25 mg/kg) and Compound 1a (60 mg/kg) exhibited significant TGI on day 22 demonstrating that a combination of a Bcl-2 inhibitor and a WEE1 inhibitor described herein can be used to treat a disease or condition described herein.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

What is claimed is:

1. A method for treating a disease or condition, wherein the disease or condition is selected from the group consisting of a hematological malignancy and a small cell lung cancer, wherein the hematological malignancy is selected from the group consisting of acute myeloid leukemia (AML) and acute lymphoblastic leukemia (ALL), comprising administering an effective amount of Compound (A), or a pharmaceutically acceptable salt thereof, and an effective amount of one or more of Compound (B), or a pharmaceutically acceptable salt thereof, wherein:

the Compound (A) has the structure:

(A)

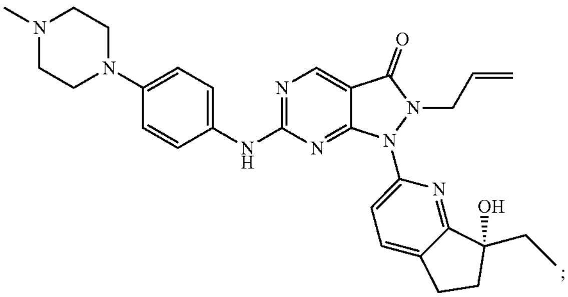
;

and the one or more of Compound (B) is a Bcl-2 inhibitor, or a pharmaceutically acceptable salt thereof;

wherein the Bcl-2 inhibitor is selected from the group consisting of venetoclax

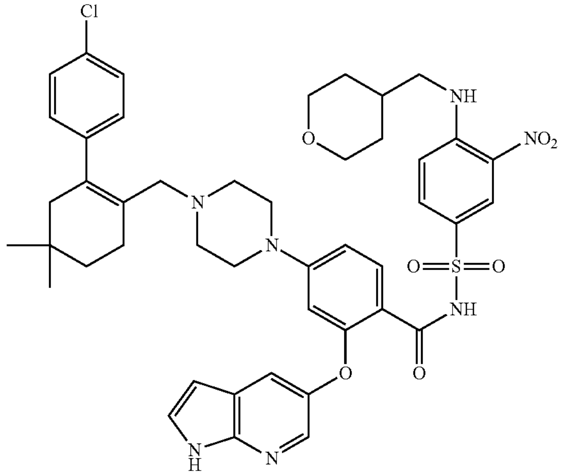 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

and navitoclax (ABT-263)

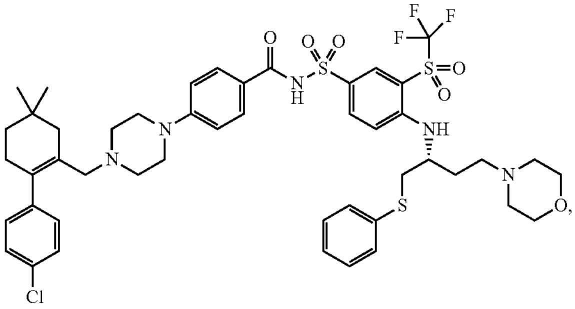 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]
, or a pharmaceutically acceptable salts of any of the foregoing.

2. The method of claim 1, wherein the disease is a hematological malignancy.

3. The method of claim 2, wherein the hematological malignancy is acute myeloid leukemia.

4. The method of claim 2, wherein the hematological malignancy is acute lymphoblastic leukemia.

5. The method of claim 1, wherein the disease or condition is small cell lung cancer.

6. The method of claim 1, wherein the Bcl-2 inhibitor is venetoclax, or a pharmaceutically acceptable salt thereof.

7. The method of claim 1, wherein the Bcl-2 inhibitor is navitoclax, or a pharmaceutically acceptable salt thereof.

8. The method of claim 1, wherein Compound (A), or a pharmaceutically acceptable salt thereof, is administered prior to Compound (B), or a pharmaceutically acceptable salt thereof.

9. The method of claim 1, wherein Compound (A), or a pharmaceutically acceptable salt thereof, is administered concomitantly with Compound (B), or a pharmaceutically acceptable salt thereof.

10. The method of claim 1, wherein Compound (A), or a pharmaceutically acceptable salt thereof, is administered subsequent to Compound (B), or a pharmaceutically acceptable salt thereof.

11. The method of claim 1, wherein Compound (A), or a pharmaceutically acceptable salt thereof, and Compound (B), or a pharmaceutically acceptable salt thereof, are administered in a single pharmaceutical composition.

12. The method of claim 1, wherein Compound (A), or a pharmaceutically acceptable salt thereof, and Compound (B), or a pharmaceutically acceptable salt thereof, are administered in separate pharmaceutical compositions.

* * * * *